(12) United States Patent
Pipper et al.

(10) Patent No.: US 8,216,855 B2
(45) Date of Patent: Jul. 10, 2012

(54) METHOD OF PROCESSING A BIOLOGICAL AND/OR CHEMICAL SAMPLE

(75) Inventors: Juergen Pipper, Singapore (SG); Tseng-Ming Hsieh, Singapore (SG); Pavel Neuzil, Singapore (SG)

(73) Assignee: Agency for Science, Technology And Research, Singapore (SG)

( * ) Notice: Subject to any disclaimer, the term of this patent is extended or adjusted under 35 U.S.C. 154(b) by 751 days.

(21) Appl. No.: 12/279,308

(22) PCT Filed: Feb. 13, 2006

(86) PCT No.: PCT/SG2006/000029
§ 371 (c)(1),
(2), (4) Date: Dec. 8, 2008

(87) PCT Pub. No.: WO2007/094739
PCT Pub. Date: Aug. 23, 2007

(65) Prior Publication Data
US 2009/0289213 A1    Nov. 26, 2009

(51) Int. Cl.
*G01N 33/553* (2006.01)
(52) U.S. Cl. ...................................................... 436/526
(58) Field of Classification Search .................... None
See application file for complete search history.

(56) References Cited

U.S. PATENT DOCUMENTS

| 5,506,121 | A | | 4/1996 | Skerra et al. ............... 435/69.7 |
| 5,854,063 | A | * | 12/1998 | Li et al. ...................... 435/287.1 |
| 5,993,665 | A | * | 11/1999 | Terstappen et al. .......... 210/695 |
| 6,103,493 | A | | 8/2000 | Skerra et al. ............... 435/69.1 |
| 6,377,387 | B1 | * | 4/2002 | Duthaler et al. ............. 359/296 |
| 2003/0083474 | A1 | | 5/2003 | Schmidt ................... 530/388.25 |
| 2003/0209560 | A1 | | 11/2003 | Hui et al. ........................ 222/1 |
| 2004/0146849 | A1 | * | 7/2004 | Huang et al. ..................... 435/4 |
| 2004/0189749 | A1 | * | 9/2004 | Araki et al. ..................... 347/48 |
| 2005/0249882 | A1 | | 11/2005 | Liu et al. ....................... 427/402 |

(Continued)

FOREIGN PATENT DOCUMENTS
JP             2-141667           5/1990
(Continued)

OTHER PUBLICATIONS

Matsuda, T, et al (2003) "Phosphorylcholine-endcapped oligomer and block co-oligomer and surface biological reactivity" Biomaterials 24: 4517-4527.*

(Continued)

*Primary Examiner* — N. C. Yang
*Assistant Examiner* — Richard Moerschell
(74) *Attorney, Agent, or Firm* — Seed IP Law Group PLLC

(57) ABSTRACT

The invention provides a method of processing a biological and/or chemical sample. The method includes providing a fluid droplet, which includes an inner phase and an outer phase. The outer phase is immiscible with the inner phase, and the outer phase is surrounding the inner phase. The inner phase includes the biological and/or chemical sample. The fluid droplet furthermore comprises magnetically attractable matter. The method also includes providing at least one surface, which is of such a texture and such a wettability for the fluid of the inner phase of the fluid droplet, that the fluid droplet remains intact upon being contacted therewith. The method further includes disposing the fluid droplet onto the at least one surface. The method also includes performing a process on the biological and/or chemical sample in the fluid droplet.

27 Claims, 15 Drawing Sheets

U.S. PATENT DOCUMENTS

| | | | |
|---|---|---|---|
| 2005/0266478 A1* | 12/2005 | Huang et al. | 435/6 |
| 2006/0257893 A1* | 11/2006 | Takahashi et al. | 435/6 |
| 2007/0003442 A1* | 1/2007 | Link et al. | 422/99 |
| 2008/0096184 A1* | 4/2008 | Brasile | 435/1.2 |
| 2008/0105829 A1* | 5/2008 | Faris et al. | 250/432 R |

FOREIGN PATENT DOCUMENTS

| | | |
|---|---|---|
| JP | 4-4869 A | 1/1992 |
| WO | WO 96/23879 | 8/1996 |
| WO | WO 99/16873 | 4/1999 |
| WO | WO 00/40712 | 7/2000 |
| WO | WO 00/75308 | 12/2000 |
| WO | WO 01/04144 | 1/2001 |
| WO | WO 03/029462 | 4/2003 |
| WO | WO 03/029463 | 4/2003 |
| WO | WO 03/029471 | 4/2003 |
| WO | WO 2004/030820 | 4/2004 |
| WO | WO 2005/019254 | 3/2005 |
| WO | WO 2005/019255 | 3/2005 |
| WO | WO 2005/019256 | 3/2005 |
| WO | 2005/069015 | 7/2005 |

OTHER PUBLICATIONS

Beste et al., "Small antibody-like proteins with prescribed ligand specificities derived from the lipocalin fold," *Proc. Natl. Acad. Sci. USA*, 96:1898-1903, Mar. 1999.

Chiriac et al., "Magnetic GMI sensor for detection of biomolecules," *J. Magnetism and Magnetic Materials*, 293:671-676, Mar. 2, 2005.

Daniel et al., "Vibration-Actuated Drop Motion on Surfaces for Batch Microfluidic Processes," *Langmuir*, 21:4240-4248, Feb. 7, 2005.

DeCory et al., "Development of an Immunomagnetic Bead-Immunoliposome Fluorescence Assay for Rapid Detection of *Escherichia coli* O157:H7 in Aqueous Samples and Comparison of the Assay with a Standard Microbiological Method," *Appl. and Environmental Microbiol.*, 71(4):1856-1864, Apr. 2005.

Domingo et al., "Preparation of PEG-grafted immunomagnetoliposomes entrapping citrate stabilized magnetite particles and their application in CD34+ cell sorting," *J. Microencapsulation*, 18(1):41-54, 2001.

Dorvee et al., "Manipulation of liquid droplets using amphiphilic, magnetic one-dimensional photonic crystal chaperones," *Nature Materials*, 3:896-899, Dec. 2004.

Gascoyne et al., "Dielectrophoresis-based programmable fluidic processors," *Lab Chip*, 4:299-309, 2004.

Guttenberg et al., "Planar chip device for PCR and hybridization with surface acoustic wave pump," *Lab Chip*, 5:308-317, 2005.

Holt et al., "Domain antibodies: proteins for therapy," *Trends in Biotechnol.*, 21(11):484-490, Nov. 2003.

Hryniewicz-Jankowska et al., "Ankyrins, multifunctional proteins involved in many cellular pathways," *Folia Histochemica Et Cytobiologica*, 40(3):239-249, 2002.

Hütten et al., "New magnetic nanoparticles for biotechnology," *J. Biotechnol.*, 112:47-63, 2004.

Kim et al., "Permanent Hydrophylic Surface Formation by Ion Assisted Reaction," *2003 ECI Conference on Heat Exchanger Fouling and Cleaning: Fundamentals and Applications*, ECI, Santa Fe, New Mexico, USA, 2004.

Li et al., "Isoelectric focusing in cyclic olefin copolymer microfluidic channels coated by polyacrylamide using a UV photografting method," *Electrophoresis*, 26:1800-1806, 2005.

Mansour, "Intracytoplasmic sperm injection: a state of the art technique," *Human Reproduction Update*, 4(1):43-56, 1998.

Matsuda et al., "Phophorylcholine-endcapped oligomer and block co-oligomer and surface biological reactivity," *Biomaterials*, 24:4517-4527, 2003.

Pollack et al., "Electrowetting-based actuation of liquid droplets for microfluidic applications," *App. Phys. Letters*, 77(11):1725-1726, Sep. 11, 2000.

Ronaghi, "Pyrosequencing Sheds Light on DNA Sequencing," *Genome Research*, 11:3-11, 2001.

Rose, "Microdispensing technologies in drug discovery," *DDT*, 4(9):411-419, Sep. 1999.

Silverman et al., "Multivalent avimer proteins evolved by exon shuffling of a family of human receptor domains," *Nature Biotechnol.*, 23(12):1556-1561, Dec. 2005.

Skerra, "Engineered protein scaffolds for molecular recognition," *J. Molecular Recognition*, 13:167-187, 2000.

Pamme, "Magnetism and microfluidics" Lab Chip 6: 24-38, 2006.

Roach et al., "Controlling Nonspecific Protein Adsorption in a Plug-Based Microfluidic System by Controlling Interfacial Chemistry Using Fluorous-Phase Surfactants" Anal. Chem. 77: 785-796, 2005.

Supplemental European Search Report, for EP06717154, mailed Jul. 30, 2010, 8 pages.

Office Action, for Japanese Application No. 2008-554204, dated Nov. 22, 2011, 6 pages. (with English Translation).

Wixforth et al., "Flatland Fluidics," *MST News*, 5:42-43, 2002.

* cited by examiner

5'-... ATCTCCCCTCCTC...-3' (sscDNA)
      3'-... GAGGAG...-5' (Sequencing primer)

3 dGTP

DNA-Polymerase                    ATP-Sulfurylase
$(DNA)_n$+dNTP ⤵ $(DNA)_{n+1}$+PPi    APS ⤵ ATP

Apyrase decomposes dNTPs and ATP
                                   Luciferase
                              Luciferin ⤵ Oxyluciferin hv~ATP~PPi~dNTP
~65 s/base                    3 hv, λ=560 nm

Fig. 21

METHOD OF PROCESSING A BIOLOGICAL AND/OR CHEMICAL SAMPLE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100139_406USPC_SEQUENCE_LISTING.txt. The text file is 1 KB, was created on Dec. 8, 2008 and is being submitted electronically via EFS-Web.

FIELD OF THE INVENTION

The present invention relates to a method for processing a biological and/or chemical sample in a fluid droplet.

BACKGROUND OF THE INVENTION

Miniaturization of devices in the chemical, pharmaceutical and biotechnological field has lead to the development of microfluidic devices that control the flow of liquid and permit the performance of a number of chemical and biological reactions. However, such devices do not allow downscaling a conventional, general-purpose chemistry laboratory onto a single microchip due to the lack of appropriate microcomponents, such as microseparators or microfilters. Furthermore, such devices do often not meet mixing requirements. Therefore, an open-well design, typically a multiwell-plate, is frequently employed in combination with automated mixing- and washing devices. However, such a well design poses increasing challenges upon further miniaturization and one of its major problems is evaporation.

The manipulation of droplets has recently received considerable interest due to the possibility of isolating and handling volumes down to the picoliter/femtoliter range (cf. e.g. international patent application WO 2004/030820). Several lab-on-a-chip (LOC), micro total analysis (μTAS), and biological microelectromechanical systems (BioMEMS) have been developed for moving, merging/mixing, splitting, and heating of droplets on surfaces, such as electrowetting-on-dielectric (EWOD) [Pollack, M. G. et al., Appl. Phys. Lett. (2000), 77, 1725-1726], surface acoustic waves (SAW) [Wixforth, A. et al., mstnews (2002), 5, 42-43], dielectrophoresis [Cascoyne, P. R. C. et al., Lab-on-a-Chip (2004), 4, 299-309], and locally asymmetric environments [Daniel, S. et al., Langmuir (2005), 21, 4240-4228]. However, these methods lack the most important operation for performing sequential biological processes: the ability to separate/purify/isolate starting material and/or reaction products from crude or complex mixtures. In order to permit such a separation a solid phase needs to be introduced as part of the droplet-based system.

Accordingly, it is an object of the present invention to provide a method for processing a chemical and/or biological sample, which avoids these discussed disadvantages.

SUMMARY OF THE INVENTION

In one aspect the present invention provides a method of processing a biological and/or chemical sample. The method includes providing a fluid droplet. The fluid droplet includes an inner phase and an outer phase. The outer phase is immiscible with the inner phase. The outer phase is surrounding the inner phase. The inner phase includes the biological and/or chemical sample. The inner phase is shielded from the environment by the outer phase. The fluid droplet furthermore includes magnetically attractable matter. The method also includes providing at least one surface. The surface is of such a texture, and such a wettability for the fluid of the inner phase of the fluid droplet, that the fluid droplet remains intact upon being contacted with the surface. The method further includes disposing the fluid droplet onto the at least one surface. The method also includes performing a process on the biological and/or chemical sample in the fluid droplet. In some embodiments the method further includes controlling the position of the fluid droplet relative to the at least one surface by exposing the fluid droplet to a magnetic or an electromagnetic field.

In a further aspect, the invention provides a fluid droplet. The fluid droplet includes an inner phase and an outer phase, and at least one magnetically attractable particle. The outer phase of the fluid droplet is immiscible with the inner phase of the fluid droplet. The outer phase of the fluid droplet is surrounding the inner phase. The inner phase of the fluid droplet is shielded from the environment by the outer phase. The at least one magnetically attractable particle includes a ligand that is capable of binding a biological and/or chemical sample.

In yet a further aspect, the invention provides a method of forming a fluid droplet. The fluid droplet includes an inner phase, an outer phase and at least one magnetically attractable particle. The method includes providing a first fluid and providing a second fluid that is immiscible with the first fluid. The method further includes contacting the first fluid and the second fluid, thereby forming a fluid droplet that includes an inner phase and an outer phase. The first fluid is forming the inner phase, surrounded by the second fluid forming the outer phase. The method further includes providing at least one magnetically attractable particle. The magnetically attractable particle includes a ligand that is capable of binding a biological and/or chemical sample. The method further includes disposing the at least one magnetically attractable particle into the fluid droplet.

BRIEF DESCRIPTION OF THE DRAWINGS

The invention will be better understood with reference to the detailed description when considered in conjunction with the non-limiting examples and the accompanying drawings, in which:

FIG. 21 illustrates the mechanism of pyrosequencing.

DETAILED DESCRIPTION OF THE INVENTION

Figure 1A:
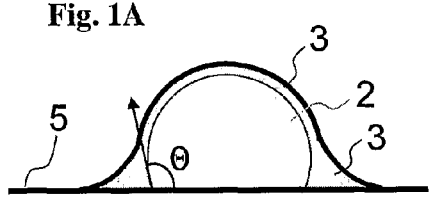
FIG. 1 depicts schematically various contact angles θ of a droplet on a surface (5), which is flat (A, B, C), convex (D) and concave (E). The droplet includes an inner phase (2) and an outer phase (3).

The present invention provides a method of processing a biological and/or chemical sample. The method is suitable for any process, in particular a process that can be performed in a fluid on a miniaturized scale (cf. below).

The sample may be of any origin. It may for instance, but not limited to, be derived from humans, animals, plants, bacteria, viruses, spores, fungi, or protozoae, or from organic or inorganic materials of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or any combination thereof may be processed in the method. Where desired, a respective sample may have been preprocessed to any degree. As an illustrative example, a tissue sample may have been digested, homogenised or centrifuged prior to being used with the device of the present invention. The sample may furthermore have been prepared in form of a fluid, such as a solution. Examples include, but are not limited to, a solution or a slurry of a nucleotide, a polynucleotide, a nucleic acid, a peptide, a polypeptide, an amino acid, a protein, a synthetic polymer, a biochemical composition, an organic chemical composition, an inorganic chemical composition, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples.

Often, but not necessarily, the sample will include, or will be expected to include, target matter or a precursor thereof. Such embodiments shall be illustrated by a number of examples: The target matter may for instance be a cell or a molecule added to or included in the sample, and it may be desired to obtain it in a purified or enriched form. As another example, the target matter may be a compound known or theorized to be obtainable from a precursor compound by means of a chemical process. In this case the sample may for instance include a solution of such a precursor compound. As further example, a cell culture media may be suspected to be contaminated. In this case, the method of the present invention may be used to identify the type of contaminant.

The target matter or precursor thereof may thus be of any nature. Examples include, but are not limited to, a nucleotide, an oligonucleotide, a polynucleotide, a nucleic acid, a peptide, a polypeptide, an amino acid, a protein, a synthetic polymer, a biochemical composition, a glycoprotein, a radioactive compound, a polyelectrolyte, a polycation, a polycatanion, a pathogen, an organic chemical composition, an inorganic chemical composition, a lipid, a carbohydrate, a combinatory chemistry product, a drug candidate molecule, a drug molecule, a drug metabolite, a cell, a virus, a microorganism or any combinations thereof. In embodiments where the target matter is for example a protein, a polypeptide, a peptide, a nucleic acid, a polynucleotide or an oligonucleotide, it may contain an affinity tag. Examples of affinity tags include, but are not limited to biotin, dinitrophenol or digoxigenin. Where the target matter is a protein, a polypeptide, or a peptide, further examples of an affinity tag include, but are not limited to, oligohistidine (such as a penta- or hexahistidine-tag), polyhistidine, a streptavidin binding tag such as the STREP-TAGS® described in US patent application US 2003/0083474, U.S. Pat. No. 5,506,121 or 6,103,493, an immunoglobulin domain, maltose-binding protein, glutathione-S-transferase (GST), calmodulin binding peptide (CBP), FLAG-peptide (e.g. of the sequence Asp-Tyr-Lys-Asp-Asp-Asp-Asp-Lys-Gly), the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the Vesicular Stomatitis Virus Glycoprotein (VSV-G) epitope of the sequence Tyr-Thr-Asp-Ile-Glu-Met-Asn-Arg-Leu-Gly-Lys, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu. Where the target matter is a nucleic acid, a polynucleotide or an oligonucleotide, an affinity tag may furthermore be an oligonucleotide tag. Such an oligonucleotide tag may for instance be used to hybridize to an immobilized oligonucleotide with a complementary sequence. A respective affinity tag may be located within or attached to any part of the target matter. As an illustrative example, it may be operably fused to the amino terminus or to the carboxy terminus of any of the aforementioned exemplary proteins.

In the method of the present invention the biological and/or chemical sample is included in a fluid droplet, such as a liquid droplet. As an illustrative example, it may be included in an inner phase of such a fluid droplet (cf. below). It may be deposited into the fluid droplet by any means (cf. below).

The method of the invention includes providing a fluid droplet. In a further aspect, the present invention also relates to a fluid droplet as described herein. As will become eminent in the following, a fluid droplet as described herein functions as a self-organising virtual reaction chamber. The fluid droplet may be of any desired volume. It may for instance have a volume in the range of about 1 pl to about 1 ml, a volume in the range of about 0.1 nl to about 500 µl, or a volume in the range of about 100 nl to 100 µl. Handling of droplets of a volume above 1 ml in air may in some embodiments require further adaptions of the droplet environment. In this regards, the skilled artisan will be aware that when using a droplet of large volume (such as e.g. 2 ml), the respective droplet may split into smaller droplets when contacting a surface. Where such splitting is undesired when carrying out the method of the invention, suitable volumes for a droplet of a selected fluid can easily be determined experimentally.

The fluid droplet includes magnetically attractable matter. Typically only one phase of the fluid droplet contains magnetically attractable matter, i.e. either the outer or the inner phase of the fluid droplet. As an illustrative example, in some embodiments a magnetic fluid such as a ferrofluid may be included in the fluid droplet. A ferrofluid is for example commercially available in form of a colloidal suspension of sub-domain magnetically attractable particles in a liquid carrier from Ferrotec (Nashua, N.H., U.S.A.). A respective ferrofluid may for instance be based on a non-polar liquid and form the outer phase of a fluid droplet. In this case the inner phase may for instance be an aqueous solution. As a further illustrative example, an iron-rich bacterium may be included in a phase of the fluid droplet. Many bacterial species contain iron as it is required for their metabolism. A large number, including *Neisseria meningitidis* and *N. gonorrhoeae*, have for example transferrin and/or lactoferrin iron-uptake systems. Such bacteria may only in certain embodiments contain sufficient iron to be used in the method of the present invention. Other bacteria reduce or oxidize iron and thus contain a higher amount thereof. An illustrative example of an (anaerobic) iron-reducing bacterium is *Geobacter metallireducens*. This bacterium may typically be included in an aqueous phase, whether the inner or the outer phase of a liquid droplet. Where the outer phase of the fluid droplet is for instance selected to be a non-polar liquid, this bacterium will typically be included in the inner phase of a respective fluid droplet (cf. also below). A respective bacterium may for instance contain, e.g. by means of recombinant expression techniques, a surface protein that is able to attract target matter.

As yet a further illustrative example, magnetically attractable particles may be included in the fluid droplet. Such particles may be able to attract target matter. In some embodiments the magnetic particles can be functionalised with specific affinity for target matter and capturing target matter, therefore acting as a binding means (see below).

For convenience magnetically attractable particles are herein referred to as "magnetic particles" or "magnetic beads". Magnetic particles may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIO-CLON, BioSource International Inc., micromod, AMBION, Merck, Bangs Laboratories, Polysciences, or Novagen Inc., to name only a few. Magnetic nanoparticles based on superparamagnetic Co and FeCo as well as ferromagnetic Co nanocrystals have been described, for example by Hütten, A. et al. (J. Biotech. (2004), 112, 47-63).

The magnetic beads may be designed to serve the function of attracting target matter through chemisorption, e.g. a covalent bond, or physisorption, e.g. electrostatic attraction. The magnetic particles used in such embodiments may provide a surface with an affinity for certain matter allowing for instance to absorb/desorb proteins, peptides, nucleic acids and other compounds. Examples include, but are not limited to, attractions by physical means, such as e.g. π-stacking, dipole-dipole, induced dipole-dipole, van-der-Waals, opposite charges, or H-bonding, e.g. antibody-antigen binding attractions, and affinity attractions formed between a ligand that has binding activity for the target matter and the target, such as for instance a ligand and a metal. As two further illustrative examples, physicochemical bonds, e.g. between gold and a thiol, or geometrical means, e.g. size exclusion, may be relied on. Different areas of the same or several magnetic particles may also be designed to attract or "capture" the target matter.

Figure 5:
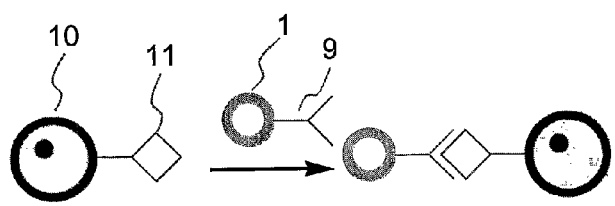
FIG. 5 illustrates schematically the isolation of target matter from a sample. A leukocyte (10) carrying a surface antigen (11) is bound by an antibody (9), coupled to a magnetically attractable particle (1).
Figure 15:
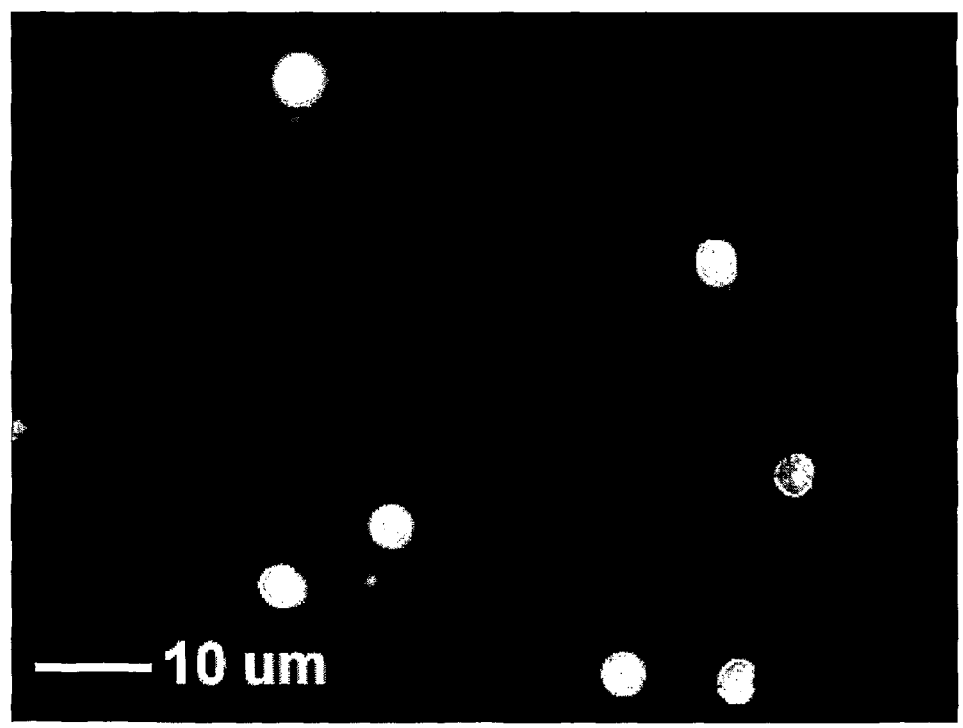
FIG. 15 depicts surface-bound fluorescein (FITC)-labelled goat anti-mouse IgG (whole molecule), covalently coupled on top of Micromer®-M superparamagnetic particles (micromod).

In some embodiments the magnetic particles include a ligand that is capable of binding target matter that is suspected or known to be included in the biological and/or chemical sample. Such a ligand may in some embodiments be capable of selectively binding such target matter such as, but is not limited to, an ion, a polyion, a metal, DNA, RNA, a protein (including a synthetic analogue thereof), bacterial cells, spores, viruses, low molecular weight organic molecules, or inorganic compounds. A respective ligand may be immobilized on the surface of the at least one magnetically attractable particle. FIG. 5 depicts schematically an example of target matter binding to a ligand immobilized on a magnetic particle. The target matter is a leucocyte carrying a cell surface marker (e.g. CD45/15). The magnetic particle includes $\gamma$-$Fe_2O_3$, $Fe_3O_4$ and polymethylmethacrylate-grafted polystyrol, immobilized thereon is an antibody directed against the cell surface marker (e.g. anti-CD45/15). FIG. 15 illustrates the binding of labelled target matter, a fluorescent antibody, to a magnetic particle.

A respective ligand may for instance be hydrocarbon-based (including polymeric) and include nitrogen-, phosphorus-, sulphur-, carben-, halogen- or pseudohalogen groups. It may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube, carbon nanofoam, a silica particle, a glass particle, or an alumosilicate. Generally, such a ligand has a higher affinity to the target matter than to other matter. Examples of a respective ligand include, but are not limited to, a crown ether, an antibody, a fragment thereof and a proteinaceous binding molecule with antibody-like functions. Examples of (recombinant) antibody fragments are Fab fragments, Fv fragments, single-chain Fv fragments (scFv), diabodies or domain antibodies (Holt, L J et al., Trends Biotechnol. 21(11), 2003, 484-490). An example of a proteinaceous binding molecule with antibody-like functions is a mutein based on a polypeptide of the lipocalin family. See for example Beste et al., Proc. Natl. Acad. Sci. USA 96, 1999, 1898-1903 and WO 99/16873, WO 00/75308, WO 03/029471, WO 03/029462, WO 03/029463, WO 2005/019254, WO 2005/019255 or WO 2005/019256. Lipocalins described in these references such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens.

Other non-limiting examples of further proteinaceous binding molecules are the so-called glubodies (see WO 96/23879), proteins based on the ankyrin scaffold (Hryniewicz-Jankowska, A et al., Folia Histochem. Cytobiol. 40, 2002, 239-249) or crystalline scaffold (WO 01/04144) the proteins described in Skerra, J. Mol. Recognit. 13, 2000, 167-187, and avimers. Avimers contain so called A-domains that occur as strings of multiple domains in several cell surface receptors (Silverman, J, et al., (2005) Nature Biotechnology, 23, 1556-1561). Further examples of a suitable ligand include, but are not limited to, a molecular imprinted structure, an extracellular matrix, a lectin, protein A, protein G, a metal, a metal ion, nitrilo triacetic acid derivates (NTA), RGD-motifs, dextranes, polyethyleneimine (PEI), polyelectrolytes, redoxpolymers, glycoproteins, aptamers, enzymes, a dye, streptavidin, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Green A binds to CoA proteins, human serum albumin, and dehydrogenases. The dyes 7-aminoactinomycin D and 4',6-diamidino-2-phenylindole bind to DNA. Cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag), the hexapeptide His-Ser-Gln-Lys-Val-Phe (binding cadmium), and N-methacryloyl-(L)-cysteine methyl ester. In addition a magnetic particle may be coated with a modifying agent that further increases the affinity of the substrate for any or a certain form, class etc. of target matter.

In some embodiments the target matter is a molecule that is suspected or known to be present within other (undesired) matter, from which it needs to be extracted. Extraction of a molecule from an organism, a part of an organism, or an embryo may for instance include the usage of a compound that facilitates the transfer of a desired molecule from an organism or a part thereof into a fluid. An illustrative example of an extraction of a molecule from a part of an organism is an extraction of proteins (wholly or partly) integrated into the cell membrane. It is often desired to transfer such proteins into an aqueous solution for further processing. A compound that facilitates the transfer of such proteins into an aqueous solution is a detergent. Contacting a respective cell membrane with an aqueous solution, to which a detergent is added, will typically result in an extraction of membrane proteins.

Where magnetic particles are used, they may at the same time as acting as a carrier for target matter, or alternatively thereto, themselves act as a tag or amplifier in the context of sensor technologies. Examples include, but are not limited to, giant magnetoresistance (GMR) [Chiriac, H, et al., (2005) Journal of Magnetism and Magnetic Materials, 293, 671-676], surface enhanced Raman spectroscopy (SERS), enhanced surface plasmon resonance (eSPR), and two-dimensional capillary electrophoresis. As an illustrative example, target matter may be bound to ligands immobilized on different magnetic particles in a fluid droplet according to the present invention. By means of further affinity ligands, whether bound on a stationary phase, in solution, or otherwise the target matter may be separated together with the magnetic particles bound thereto. Where the magnetic particles are exposed to a magnetic field, they develop a dipole field. This dipole field may be detected by a dipole sensor. By quantifying the amplitude of the sensor impedance the amount of target matter can be quantified.

The fluid droplet further includes an inner phase and an outer phase. The outer phase is surrounding the inner phase. In some embodiments the outer phase is a bulk phase accommodating the inner phase. In other embodiments the outer phase is surrounding the inner phase as a film. The fluid of the outer phase may be a liquid or a gas. The fluid of the inner phase is typically a liquid.

In embodiments where the outer phase is a film, it is typically of a volume that is in the range of several magnitudes below to several magnitudes above the volume of the inner phase. The volume ratio of the inner to the outer phase may for example be selected in the range of about 1000:1 to about 1:1000, such as the range of about 10:1 to about 1:10. As an example, for applications involving one or more liquid droplets at room temperature it may be desired to chose a high volume ratio of the inner to the outer phase, for instance a ratio of about 1000:1. For applications involving one or more liquid droplets in the range of about 100° C. it may be desired to choose a low volume ratio of the inner to the outer phase, for instance a ratio of about 1:1000. In some embodiments a respective film is furthermore of uniform thickness. In other embodiments the film includes irregularities such as a cone. Respective irregular interfaces are for instance known for interfaces between water and some ionic liquids such as octylsubstituted hexafluorophosphates.

The outer phase is immiscible with the inner phase. Typically, the fluid of the outer phase is immiscible with the fluid of the inner phase. Any fluid may be used for the respective phase, as long as it is (a) immiscible with the other phase, so that two separate phases can form, and (b) the fluid does not prevent the desired process from being carried out. An illustrative example of two immiscible gases are helium and carbon dioxide, which generally form two immiscible phases over extended composition ranges, as long as the temperature is below the critical point of the binary mixture and the pressures is above the vapour pressure of pure liquid carbon dioxide. The process is typically carried out in the inner phase (cf. also below). Thus a selected fluid may be of any property. In case a phase is selected to be a liquid or a gas, it may for instance be a polar or a non-polar liquid or gas, respectively. Often liquids are classified into polar and non-polar liquids in order to characterize properties such as solubility and miscibility with other liquids. Polar liquids typically contain molecules with an uneven distribution of electron density. The same classification may be applied to gases. The polarity of a molecule is reflected by its dielectric constant or its dipole moment. Polar molecules are typically further classified into protic and non-protic (or aprotic) molecules. A fluid, e.g. a liquid, that contains to a large extent polar protic molecules may therefore be termed a polar protic fluid. A fluid, e.g. a liquid, that contains to a large extent polar non-protic molecules may be termed a polar non-protic fluid. Protic molecules contain a hydrogen atom which may be an acidic hydrogen when the molecule is dissolved for instance in water or an alcohol. Aprotic molecules do not contain such hydrogen atoms.

Examples of non-polar liquids include, but are not limited to, hexane, heptane, cyclohexane, benzene, toluene, dichloromethane, carbon tetrachloride, carbon disulfide, dioxane, diethyl ether, or diisopropylether. Examples of dipolar aprotic liquids are methyl ethyl ketone, chloroform, tetrahydrofuran, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide. Examples of polar protic liquids are water, methanol, isopropanol, tert.-butyl alcohol, formic acid, hydrochloric acid, sulfuric acid, acetic acid, trifluoroacetic acid, dimethylarsinic acid $[(CH_3)_2AsO(OH)]$, acetonitrile, phenol or chlorophenol. Ionic liquids typically have an organic cation and an anion that may be either organic or inorganic. The polarity of ionic liquids (cf. below for examples) is known to be largely determined by the associated anion. While e.g. halides, pseudohalides, $BF_4^-$, methyl sulphate, $NO_3^-$, or $ClO_4^-$ are polar liquids, hexafluorophosphates, $AsF_6^-$, bis(perfluoroalkyl)-imides, and $[C_4F_6SO_3]^-$ are non-polar liquids. Each phase may also contain more than one fluid. If for example more than one liquid is used for the inner or the outer phase, the selected mixture of the liquids is still capable of forming a phase separate from the respective other phase of the droplet, and the liquids are generally miscible with each other in the selected ratio. As an illustrative example, ammonia, a polar gas, readily dissolves in water, a polar liquid, so that these two fluids may be included in a common phase.

Two immiscible phases may for instance be obtained where a polar fluid, such as a hydrophilic liquid (cf. below), is selected for one phase and non-polar fluid, such as a hydrophobic liquid, is selected for the other phase. As an illustrative example, carbon dioxide ($CO_2$), a non-polar gas, does not dissolve (except for trace amounts) in water, a polar liquid. Under certain circumstances, such as under increased pressure, carbon dioxide may however be dissolved in water (cf. e.g. carbonated drinks). In some embodiments the fluid of the inner phase may be a polar liquid and the fluid of the outer phase of the fluid droplet may be a non-polar liquid. Suitable polar liquids include, but are not limited to, water, deuterium oxide, tritium oxide, an alcohol, an organic acid (including a salt thereof), an inorganic acid (including a salt thereof), an ester of an organic acid, an ester of an inorganic acid, an ether, an amine (including a salt thereof), an amide, a nitrile, a ketone, an ionic detergent, a non-ionic detergent, carbon dioxide, dimethyl sulfone, dimethyl sulfoxide, a thiol, a disulfide, and a polar ionic liquid. Suitable non-polar liquids include, but are not limited to, a mineral oil, a silicone oil, a natural oil, a perfluorinated carbon liquid, a partially halogenated, e.g. fluorinated, carbon liquid, an alkane, an alkene, an alkine, a cycloalkane, an aromatic compound, carbon disulfide and a non-polar ionic liquid.

As an illustrative example, the fluid of the inner phase of the fluid droplet may be hydrophilic liquid and the fluid of the outer phase of the fluid droplet may be a hydrophobic liquid. Hydrophilic ("water-loving") liquids, also termed lipophilic ("fat-loving"), contain molecules which can form dipole-dipole interactions with water molecules and thus dissolve therein. Hydrophilic ("water-hating") liquids, also termed lipophobic, have a tendency to separate from water. Examples of a hydrophilic liquid include, but are not limited to water, acetone, methanol, ethanol, propanol, isopropanol, butanol, tetrahydrofuran, pyridine, chloroform, ethylene glycol monobutyl ether, pyridine, ethyl acetate, acetonitrile, dimethylformamide, N,N-dimethyl acetamide, N-methylpyrrolidone, formic acid, formamide, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoroethyl)phosphinate, 1-butyl-3-methylimidazolium tetrakis(3,5-bis(trifluoromethylphenyl)

borate, tetrabutyl-ammonium bis(trifluoromethyl)-imide, ethyl-3-methylimidazolium trifluoromethanesulfonate, 1-butyl-3-methylimidazolium methylsulfate, 1-n-butyl-3-methylimidazolium methylsulfate, 1-butyl-3-methylimidazolium ([bmim]) octylsulfate, and 1-n-butyl-3-methyl-imidazolium tetrafluoroborate. Examples of a non-polar liquid include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)-sulfonyl]amide bis(triflyl)amide, 1-ethyl-3-methylimidazolium bis[(trifluoromethyl)-sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis-(trifluoromethylsulfonyl)imide, trihexyl(tetradecyl) phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris (pentafluoroethyl)trifluorophosphate, trihexyl-(tetradecyl) phosphonium, N"-ethyl-N,N,N',N-tetramethylguanidinium, 1-butyl-1-methyl pyrrolidinium tris(pentafluoroethyl) trifluorophosphate, 1-butyl-1-methyl pyrrolidinium bis(trifluoromethylsulfonyl) imide, 1-butyl-3-methyl imidazolium hexafluorophosphate, 1-ethyl-3-methylimidazolium bis(trifluoromethylsulfonyl)imide and 1-n-butyl-3-methyl-imidazolium.

A phase of the fluid droplet may include further matter, for example dissolved, emulsified or suspended therein. As an illustrative example, where an aqueous phase is used, it may include one or more buffer compounds. Numerous buffer compounds are used in the art and may be used to carry out the various processes described herein. Examples of buffers include, but are not limited to, solutions of salts of phosphate, carbonate, succinate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methylamino]-1-ethansulfonic acid (also called TES), 2-cyclohexylamino-ethansulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, ethylamine, triethylamine, glycine, glycylglycine, histidine, tris(hydroxymethyl)aminomethane (also called TRIS), bis-(2-hydroxyethyl)-imino-tris(hydroxymethyl)methane (also called BIS-TRIS), and N-[Tris(hydroxymethyl)-methyl]-glycine (also called TRICINE), to name a few. The buffers may be aqueous solutions of such buffer compounds or solutions in a suitable polar organic solvent. As an illustrative example, a buffer may be deposited in solid form, for example freeze-dried. In such a case the solid buffer, e.g. a powder, may be dissolved in an aqueous phase by merging and or mixing, for instance assisted or performed by means of ultrasound. In such a case the amount of volume of a respective aqueous phase used may for instance be used to obtain the desired final buffer concentration.

Further examples of matter included in a phase of the fluid droplet include, but are not limited to, reagents, catalysts and reactants, for carrying out a chemical or biological process. As an illustrative example, salts, substrates or detergents may be added in order to maintain cells or proteins in an intact state. As a further illustrative example, chelating compounds may be required, for instance to protect organisms from traces of otherwise toxic salts or to increase the yield of a chemical reaction. As yet further illustrative examples, protease, RNase, or DNase inhibitors may be added in order to maintain proteins, RNA, or DNA in an intact state. A further example of a possible additive to a phase of the fluid droplet includes magnetically attractable particles (see above).

The inner phase of the fluid droplet is shielded from the environment by the outer phase. The outer phase may thus for example act as a barrier or as a seal. The term "environment" refers to any fluid or solid matter, such as for instance a gas (of any desired density or pressure) or a liquid, which is not part of the inner phase, the outer phase or a surface, on which the fluid droplet is disposed. As an illustrative example, the outer phase may prevent or reduce evaporation of the inner phase into surrounding air. As a further example, the outer phase may provide a barrier in terms of contact or diffusion etc. The outer phase may for instance prevent contact with solid matter such as sand or dust particles or with fluid that would be miscible with the inner phase of the fluid droplet. The outer phase of the droplet may also provide access of energy, such as electromagnetic radiation of a certain wavelength to the inner phase. The outer phase may also serve in protecting a surface at which the fluid droplet is positioned against contamination by components of the inner phase of the fluid droplet. Furthermore, the outer phase may enable a sample such as a body liquid, e.g. blood, sputum, etc. to move on a non-polar surface (e.g. PTFE). In some embodiments the outer phase may also maintain sterility of the inner phase, even where the fluid droplet as a whole is being handled under, or exposed to, non-sterile conditions. The outer phase may furthermore allow for the contact and fusion with another fluid droplet that includes two phases of similar polarities (e.g. similar hydrophobicities). As an example, where the outer phase is a hydrophobic liquid and the inner phase is a hydrophilic liquid, the outer phase may be capable of merging with the outer phase of a further fluid droplet that is hydrophilic and surrounds an inner phase that is hydrophilic. In such a case a spontaneous fusion of the two exemplary droplets may occur.

The fluid droplet may be provided by any means. Forming the fluid droplet includes providing the fluid of the inner phase, providing the fluid of the outer phase and providing the sample. The fluid droplet that includes two phases, as used in the present invention, is a self-organizing system, the formation of which is driven by surface energy. Accordingly the inner or the outer phase, or the sample may be provided first, in a second or in a final step. Alternatively any one or more (or parts) of the inner phase, the outer phase, or the sample may be provided simultaneously. As an illustrative example, forming the fluid droplet may include providing a first fluid and providing a second fluid that is immiscible with the first fluid. Forming the fluid droplet may further include dispensing an aliquot, for instance a droplet, of the first fluid onto the second fluid, thereby forming one or more fluid droplet(s) of the first fluid surrounded by the second fluid, thereby forming one or more fluid droplets comprising an inner phase and an outer phase. In some embodiments forming the fluid droplet may also include collecting the droplet of said first fluid, or a part thereof, out of said second fluid that is forming the outer phase. In this case a droplet may be formed that includes an outer phase surrounding the inner phase as a film. In some embodiments an initial larger droplet can be formed by forming a fluid droplet of the first fluid in the second fluid. In these embodiments, from this initial larger droplet several smaller droplets can then be collected. Due to fluid droplet being a self-organizing system, there are generally no additional means required in order to achieve a respective portioning of an initial volume.

In this respect the present invention also relates to a method of forming a fluid droplet as defined above. The method includes forming a fluid droplet as just described, i.e. by providing two fluids immiscible with each other, contacting the first fluid and the second fluid, thereby forming a fluid droplet of a first fluid surrounded by a second fluid (supra). In one embodiment of the method, contacting the first and the second fluid includes dispensing a droplet of the first fluid into the second fluid. In some embodiments the method may also include collecting the droplet of the first fluid out of the second fluid, thereby forming a fluid droplet that includes an inner phase and an outer phase, the latter surrounding the inner phase as a film. The first fluid forms the inner phase, the second fluid the outer phase. The method further includes providing at least one magnetically attractable particle, which includes a ligand that is capable of binding target matter (supra). The method also includes disposing the at least one magnetically attractable particle into the first fluid forming the inner phase of the fluid droplet. As indicated above, the at least one magnetically attractable particle may be disposed into the first or the second fluid at any time during this method, since the fluid droplet is a self-organising system. A magnetic particle may for example be disposed into the droplet, for example into the first fluid, before the droplet of the first fluid is dispensed into the second fluid.

Figure 1B:
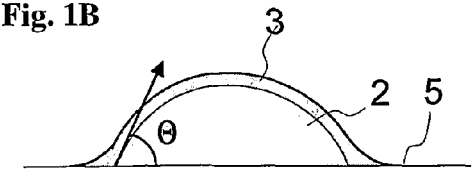
Figure 1C:
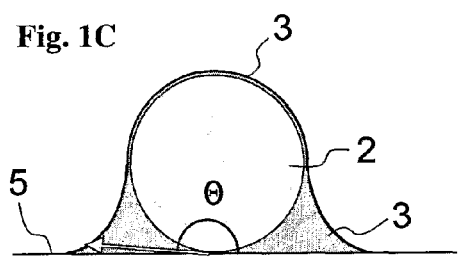
Figure 1D:
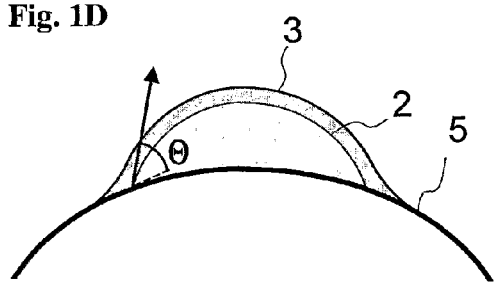
Figure 1E:
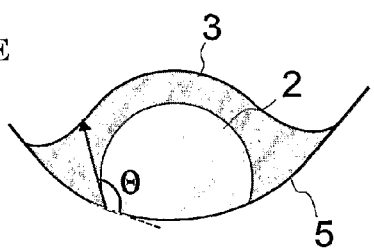
Figure 2A:
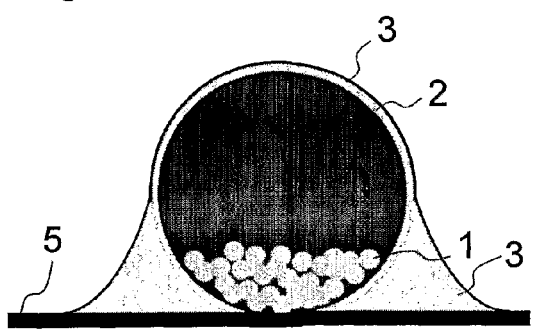
FIG. 2 depicts a droplet of a high contact angle θ on a surface (5) in side view (A) and top view (B). The droplet includes an inner phase (2) and an outer phase (3). The droplet also includes magnetically attractable particles (1).
Figure 2B:
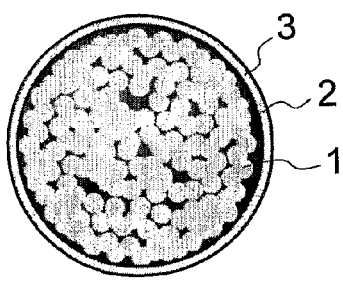
Figure 4A:
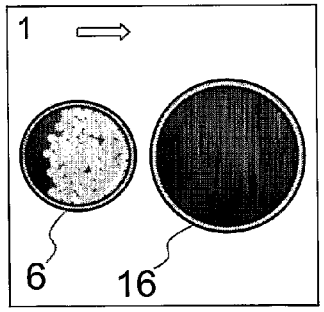
FIG. 4 depicts a washing process (cf. also FIG. 18) of a sample in a droplet (6) by means of a second droplet (16) in top view (A) as well as side view (B), depicting a magnet (20) under a surface (5). A second droplet involved in a washing process may be located at a surface that differs from the surface (5), at which the fluid droplet that includes magnetic particles (1), and an inner (2) and an outer phase (3) is located (C).
Figure 4A:
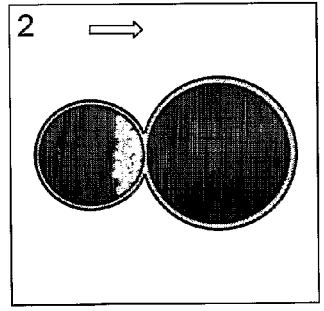
Figure 4A:
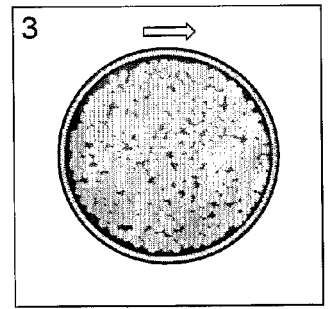
Figure 4A:
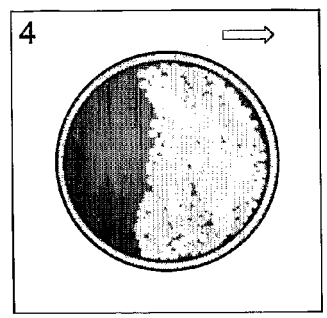
Figure 4A:
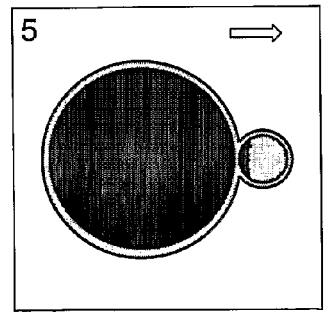
Figure 4A:
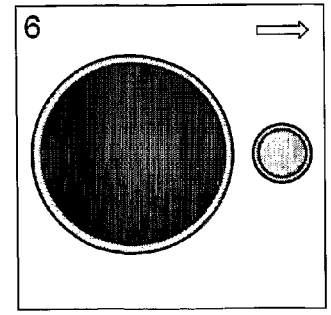
Figure 4B:
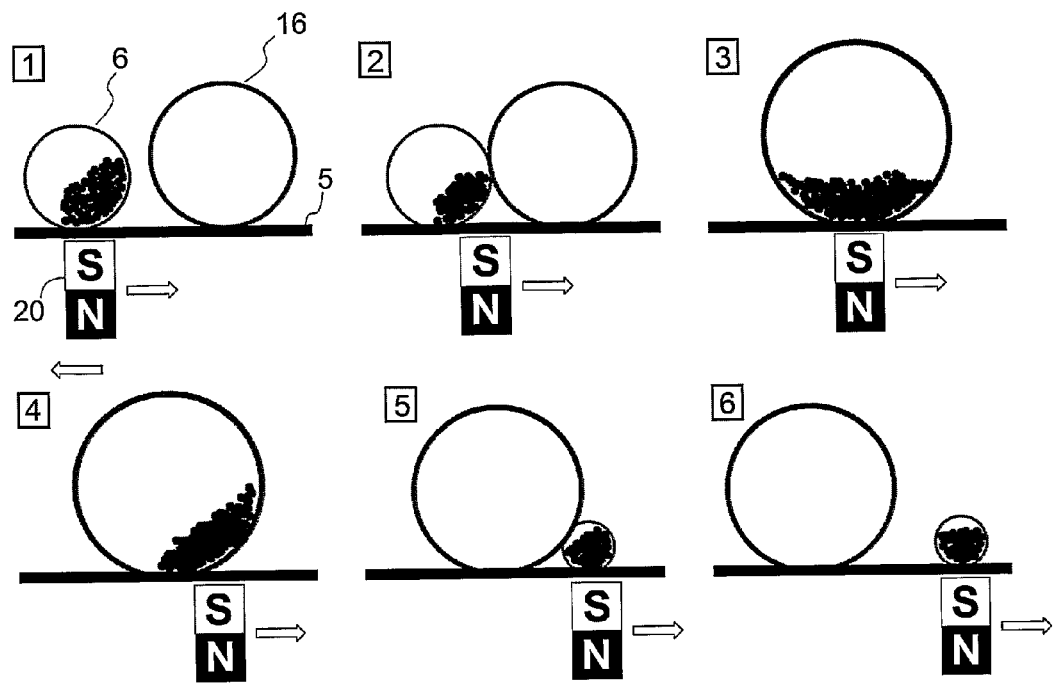
Figure 4C:
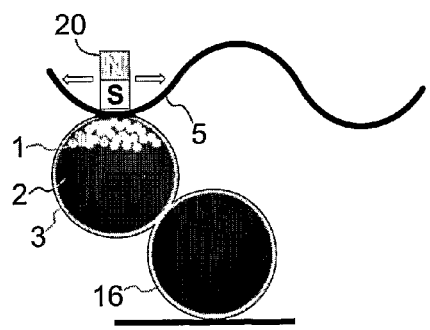

As mentioned above, the inner phase of the droplet may directly contact matter that is included in at least one surface on which the droplet is or is intended to be disposed. Two illustrative examples of such matter are a solid surface or the surface of a fluid. The at least one surface may have any shape and geometry as long as it is of such a texture, e.g. roughness and waviness, that the fluid droplet remains intact upon being contacted therewith. As an illustrative example, it will typically be required to provide a surface with a roughness for the fluid of the inner phase of the fluid droplet that is low enough to allow a fluid droplet that gets in contact therewith to remain intact. The term "intact" refers to the existence of a defined droplet including two phases. The fluid droplet is thus understood to remain intact, while it is for instance spread to a desired extend, or merged with another droplet. The at least one surface may for example be concave or convex rounded (cf. FIGS. 1D and 1E) or a combination thereof (FIG. 4C). In one embodiment the at least one surface is essentially flat (cf. e.g. FIGS. 1A-1C). In another embodiment the at least one surface has the form of a cylinder, along the surface of which a droplet may be rotated.

The method of the present invention includes providing at least one surface, such as e.g. described above. In some embodiments more than one surface is provided, such as for instance two, three, four etc. surfaces. In one embodiment at least two surfaces are facing each other. The surface(s) may be of any material as long as it is of such a wettability for the fluid of the inner phase of the fluid droplet that the fluid droplet remains intact upon being contacted therewith. In one embodiment where more than one surface is provided, for instance two surfaces facing each other, all respective surfaces are of such a texture and such a wettability for the fluid of the inner phase that the fluid droplet remains intact upon being contacted therewith.

Where for instance the inner phase of the fluid droplet is a polar liquid, such as an aqueous fluid, the at least one surface may be non-polar. In one embodiment the inner phase of the fluid droplet is an aqueous fluid, e.g. water, and the at least one surface is non-polar. A respective non-polar surface may in some embodiments be selected from the group consisting of silicone (including surface-modified silicone), a polymer such as plastic (whether a biopolymer or a synthetic polymer, including a partially fluorinated polymer, a perfluorinated polymer, and a surface-modified polymer), surface-modified silicon oxide, surface-modified silicon hydride, surface-modified paper, surface-modified glass such as e.g. surface-modified pyrex, surface-modified quartz, surface-modified glimmer, surface-modified metal, surface-modified alloy, surface-modified metal oxide, surface-modified ceramic, and any composite thereof. As a further illustrative example, the inner phase of the fluid droplet may be hydrophilic and the at least one surface may be hydrophobic or oleophobic. As yet another illustrative example, the inner phase of the fluid droplet may be non-polar and the at least one surface may be polar.

A surface modification is typically obtained by a treatment carried out to alter characteristics of a solid surface. Such a treatment may include various means, such as physical, e.g. mechanical, thermal, or electrical means, chemical means, or electrochemical means. As an example, a surface of plastic materials can be rendered hydrophilic via treatment with dilute sulfuric acid, chromic acid, a solution of potassium permanganate, or dilute nitric acid. As another example, a polydimethylsiloxane (PDMS) surface can be rendered hydrophilic by an oxidation with oxygen or air plasma. The surface of a hydrophobic polymer, such as polymethylmethacrylate, polytetrafluoroethylene, polyethylene terephthalate, and polycarbonate, may also be rendered hydrophilic by means of ionic radiation in the presence of a reactive gas, as described by Kim et al (2003 ECI Conference on Heat Exchanger Fouling and Cleaning: Fundamentals and Applications [2003], Vol. RP1, 107-114). Silicon may be rendered hydrophilic by dipping in $H_2O/H_2O_2/NH_4OH$. Furthermore, the surface properties of any hydrophobic surface can be rendered more hydrophilic by coating with hydrophilic self-assembled monolayers, a hydrophilic polymer or by treatment with surfactants or plasma treatment with polymeric precursors.

Where a method according to the present invention is to be combined with another method such as an analytical or preparative method (see also below), it may be desired to provide a surface that allows, or is advantageous for, carrying out both such a further method and a method according to the present invention. During, or before, carrying out such a further method the integrity of the two phases of the fluid droplet may be affected or degraded. As a consequence matter that is located in the inner phase of the fluid droplet may be exposed to another fluid phase and contact the surface. The availability of various suitable inner and outer phases for the fluid droplet used in the present invention typically allows for a flexible selection of a chemical surface treatment, including a coating. Therefore often the same surface can be used during both the method of the present invention and a subsequent method.

As an illustrative example, it may be desired to perform an electrophoretic separation or an isoelectric focussing, for instance by subjecting the magnetic particles, whether included in the fluid droplet used in the present invention or not, thereto. It may for instance be desired to provide a surface with minimal interactions for any matter present, which is detectable by the selected method. Where it is for instance desired to analyse the purity of an isolated protein by applying an electromagnetic field (such as an electrophoretic method), analysis results may be falsified by a surface that significantly interacts with proteins. Two illustrative example of a suitable surface coating with minimal protein interactions are the polar polymer poly-N-hydroxyethylacrylamide and poly(ethylene glycol)-terminated alkyltrichlorosilane. It is likewise known that the properties of a surface of a device used for isoelectric focusing affect the efficiency for obtaining narrow isolated zones during both the focusing and mobilization processes. Examples of surface treatments that may be used to achieve a high separation using a pH gradient in isoelectric focusing include, but are not limited to, a highly polar polymer coating such as polyacrylamide, polyvinylpyrrolidone, polyethylene glycol, poly(vinyl) alcohol, or a fluorocarbon coating.

Examples of a chemical surface treatment include, but are not limited to exposure to, or reaction with, hexamethyldisilazane, 2-hydroxy-4-(3-triethoxysilylpropoxy)diphenylketone, 3-triethoxysilyl)propylsuccinic anhydride, 2-[methoxy(poly-ethyleneoxy)propyl]trimethoxysilane, (heptadecafluoro-1,1,2,2-tetrahydrodecyl)triethoxysilane, (tridecafluoro-1,1,2,2-tetrahydrooctyl)triethoxysilane, (heptadecafluoro-1,1,2,2-tetrahydrodecyl)trichloro-silane, (tridecafluoro-1,1,2,2-tetrahydrooctyl)trichlorosilane, methacroyloxymethyltris(trimethylsiloxy)silane, PlusOne™ Repel-Silane ES (a 2% solution of dimethyldichlorosilane dissolved in octamethyl cyclo-octasilane, GE Healthcare), SIGMA-Cote° (a chlorinated organopolysiloxane in heptane), 3-mercaptopropyltrimethoxysilane, octadecylsilane, octadecyltrimethoxysilane, epoxypropoxypropyltrimethoxysilane, 2-(diphenylphosphino)ethyltriethoxysilane, bis(2-hydroxyethyl)-3-aminopropyl-triethoxysilane, aminobutyltriethoxysilane, (3-acryloxypropyl)trimethoxysilane, trimethylchlorosilane, dimethyldichlorosilane, propyltrichlorosilane, tetraethoxysilane, glycidoxypropyltrimethoxysilane, 3-aminopropyltriethoxysilane, 2-(3,4-epoxy cyclohexyl)ethyltrimethoxysilane, 3-(2,3-epoxy propoxyl)propyltrimethoxysilane, polydimethylsiloxane (PDMS), γ-(3,4-epoxycyclohexyl)ethyltrimethoxysilane, poly(methyl methacrylate) or a polymethacrylate co-polymer, urethane, polyurethane, fluoropolyacrylate, Teflon AF 1600, 2400, and 2200, poly(acrylic acid) (PAA), poly(methoxy polyethylene glycol methacrylate), poly(dimethyl acrylamide), poly N-acroyl-aminoethoxyethanol (AAEE), polyacrylamide grafted with benzophenone and Pluronic-F-68 (Li et al., Electrophoresis 2005, 26, 1800-1806), poly[N-(2-hydroxypropyl) methacrylamide] (PHPMA), α-phosphorylcholine-o-(N,N-diethyldithiocarbamyl)undecyl oligoDMAAm-oligo-STblock co-oligomer (cf. e.g. Matsuda, T et al., Biomaterials, (2003), 24, 4517-4527), poly(3,4-epoxy-1-butene), 3,4-epoxy-cyclohexylmethylmethacrylate, 2,2-bis[4-(2,3-epoxy propoxy) phenyl]propane, 3,4-epoxy-cyclohexylmethylacrylate, (3',4'-epoxycyclohexylmethyl)-3,4-epoxycyclohexyl carboxylate, di-(3,4-epoxycyclohexylmethyl)adipate, a copolymer of polyethyleneglycol and polypropyleneglycol such as UCON (Analabs, Norwalk, Conn., USA), bisphenol A (2,2-bis-(p-(2,3-epoxy propoxy) phenyl) propane), 2,3-epoxy-1-propanol, polyvinylalcohol, polyvinyl pyrrolidone, dextran, surfactants such as dodecyldimethyl (3-sulfopropyl) ammonium hydroxide ($Cl_2N_3SO_3$), hexadecyldimethyl (3-sulfopropyl) ammonium hydroxide ($C_{16}N_3SO_3$), and coco (amidopropyl)hydroxyl dimethylsulfobetaine (RCONH $(CH_2)_3N^+(CH_3)_2CH_2CH(OH)CH_2SO_3^-$ with R=$C_8$-$C_{18}$), including a polymer surfactant such as e.g. Supelcoat PS2 (Supelco, Bellefonte, Pa., USA), methylcellulose, hydroxypropylcellulose, hydroxyethylcellulose, or hydroxypropylmethylcellulose. A coating with a polymer may for instance be carried out by means of chemical vapour deposition or by polymerisation on the surface following an exposure of the surface to a difunctional reagent, as disclosed in US patent application 2005/0249882. In the latter case a stable covalent linkage between the surface and the polymer coating is generated. It may for example be desired to select this technique in embodiments where the surface is rough or contains micro- or nanocavities.

Furthermore, the at least one surface may provide areas of different surface characteristics. In the above illustrative example of an inner phase of the fluid droplet being a polar (e.g. hydrophilic) liquid, some areas of the surface may for example be more non-polar (e.g. hydrophobic) than others, or some regions may be polar (e.g. hydrophilic). As an illustrative example, a surface area of increased polarity may be desired to achieve a spreading of a droplet on a DNA-array for hybridization. Any part of the at least one surface may also be treated in such a way that it provides respective polar or non-polar surface characteristics. For example a solid surface may be treated respectively.

A common way of defining the wettability of a surface for a fluid such as a liquid is the contact angle (also termed wetting angle) between a droplet of the fluid in thermal equilibrium on a horizontal surface, which is generally smooth and homogeneous, typically surrounded by a gas such as air. In this respect, a person skilled in the art will be aware of the fact that an increasing roughness of a surface typically increases the contact angle.

Depending on the type of surface and fluid, the droplet may have a variety of shapes as illustrated in FIG. 1. FIG. 1 also shows the respective contact angle θ of the inner phase of the depicted fluid droplets. This contact angle is generally determined individually for each respective phase of interest (cf. below), for instance the inner phase and the outer phase of a fluid droplet to be used in the present invention. In some embodiments the wettability of a surface for a fluid droplet that includes an inner phase and an outer phase, may be determined in the same way, in particular where the outer phase is a bulk phase. It is however more convenient to determine the contact angle of each phase separately. A contact angle θ is given by the angle between the interface of the droplet and the horizontal surface. Such a contact angle θ is a thermodynamic variable that depends on the interfacial tensions of the surfaces involved. It reflects the balance of forces exerted by an attraction of molecules within the droplet to each other versus the attraction or repulsion those droplet molecules experience towards the surface molecules.

The most commonly used technique of determining the contact angle is the so called static or sessile drop method in a configuration of a single phase, resembling the inner phase as shown in FIG. 1. The measurement usually involves a successive addition of fluid droplets until a plateau in the contact angle is reached. The value at a respective plateau is called the advancing contact angle. A further value that is regarded as less meaningful in this respect is the so called receding contact angle. It is obtained by continuing an advancing contact angle experiment by immediately subsequently monitoring the contact angle as equivalent volume droplets of fluid are successively retracted from the droplet. Further means of determining the contact angle include the Wilhemly Plate method, the Captive Air Bubble method, the Capillary Rise method, and the Tilted-drop measurement.

A contact angle θ of zero results in wetting, while a contact angle θ between about 0 and about 90 results typically in spreading of the fluid droplet, in particular at values in the range below about 45 degrees. Contact angles θ greater than about 90 indicate the fluid tends to bead or shrink away from the solid surface (cf. FIG. 1C for an example). As already indicated above, the contact angle is typically determined for a single phase of fluid. Accordingly the contact angle of the inner and the outer phase of the fluid droplet are typically determined separately. In some embodiments the at least one surface used in the present invention is of a wettability for the fluid of the inner phase of the fluid droplet that a fluid droplet of a single phase, consisting of the respective fluid, when disposed thereon can be characterized by an advancing contact angle θ of about 50 degrees or higher. Thus, the wettability of the surface is characterized by an advancing contact angle θ at the interface of a fluid droplet, which is made up of the inner phase of the above defined fluid droplet, with the at least one surface of about 50 degrees or higher. In some embodiments the at least one surface used in the present invention is of a wettability for the fluid of the outer phase of the fluid droplet that a fluid droplet consisting of the fluid of the outer phase is characterized by an advancing contact angle θ at the interface of a respective fluid droplet with the at least one surface of about 50 degrees or higher. In some embodiments the at least one surface used in the present invention is of a wettability for the fluid droplet as a whole that is so low that it is characterized by an advancing contact angle θ at the interface of said fluid droplet with the at least one surface of about 50 degrees or higher.

In some embodiments the surface, e.g. a solid surface, is furthermore inert against the fluid of the inner or the outer phase of the fluid droplet. Such embodiments allow for multiple reusing of the device. An illustrative example of a material that is inert against most corrosive media is a fluoropolymer such as fluoroethylenepropylene (FEP), polytetrafluoroethylene (PFTE, Teflon), ethylene-tetrafluoroethylene (ETFE), tetrafluoroethylene-perfluoro-methylvinylether (MFA), vinylidene fluoride-hexafluoro-propylene copolymer, tetrafluoroethylene-hexafluoropropylene copolymer, vinylidene fluoride-hexafluoropropylene-tetrafluoroethylene terpolymer, perfluoromethyl vinyl ether-tetrafluoroethylen copolymer, perfluoroalkoxy copolymer (PFA), poly (vinyl fluoride), polychlorotrifluoroethylene, fluorosilicones, or fluorophosphazenes.

Additionally, and in particular where a respective phase is a liquid phase, the inner or the outer phase of the fluid droplet may include an ionic or non-ionic surfactant, for example a perfluorocarbon-surfactant. Typically the surfactant adsorbs primarily at the solid-liquid and liquid-liquid and liquid-vapour interfaces near the contact line region, where applicable. As an illustrative example, it may be desired to use a surfactant in order to reduce nonspecific interactions of a sample included in the inner phase of the fluid droplet with a surface. Numerous surfactants, which are partly hydrophilic and partly lipophilic, are used in the art, such as for instance alkyl benzene sulfonates, alkyl phenoxy polyethoxy ethanols, alkyl glucosides, secondary and tertiary amines such as diethanolamine, Tween, Triton 100 and triethanolamine, or e.g. fluorosurfactants such as ZONYL® FSO-100 (DuPont).

The method of the present invention also includes disposing the fluid droplet onto the at least one surface. The fluid droplet may be disposed by any means. As an example, a dispenser may be provided. A dispenser may employ any suitable device or mechanism in order to provide and dispense a fluid droplet of a desired size. Examples include, but are not limited to, piezoelectric pipettors, syringe pump-based pipettors, peristaltic pumps, touch-off dispensing, pressure-mediated dispensing, inkjet dispensing (including syringe-solenoid dispensing), pin-transfer (cf. Rose, D, Drug Discovery Today (1999), 4, 411-419 for a review). Disposing the fluid droplet may also rely on, or be assisted by, the properties of the magnetically attractable matter included therein. Accordingly, a magnetic, electromagnetic, electrical or electrostatic field may be used. As an illustrative example, a magnetic plug may be injected from a capillary under the influence of a magnetic, electromagnetic or electrical field, for instance by dielectrophoresis. By means of the dispenser the fluid droplet may in one embodiment be disposed onto the surface without contacting the same. In yet another embodiment the fluid droplet may be dispensed directly onto a surface by means of contact dispensing. Where desired, the dispensed quantities may be measured, e.g. by means of a camera as disclosed in US patent application 2003/0209560.

Figure 3A:
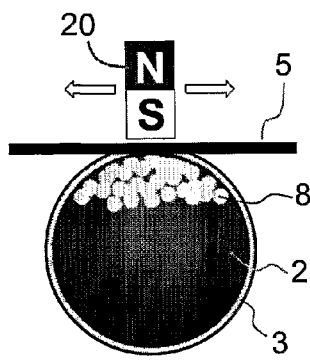
FIG. 3A shows a droplet of an inner phase (2) and an outer phase (3) that includes functionalized magnetically attractable particles (8) in side view. The position of the droplet below a surface (5) is controlled by means of a permanent magnet (20), in a position relative to the surface (5).
Figure 3B:
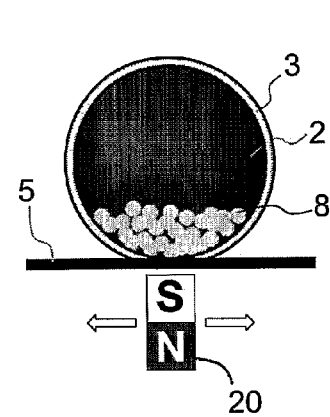
FIG. 3B shows a droplet (6) of an inner phase (2), an outer phase (3) and magnetically attractable particles (8) on top of a surface (5).
Figure 3C:
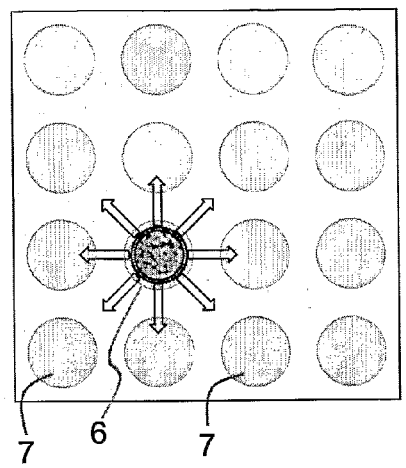
FIG. 3C shows a droplet (6) as depicted in FIG. 3A or 3B on an electromagnet (7), which is a member of an array of electromagnets seen from above or below respectively.
Figure 7:
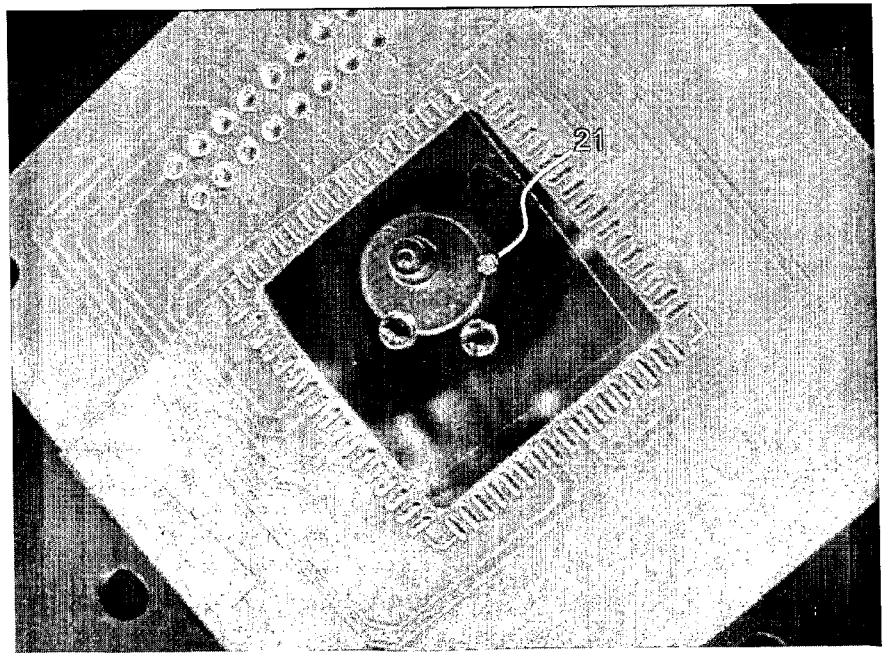
FIG. 7 depicts the isolation of white blood cells (WBCs), starting from 0.1 µl fresh capillary whole human blood, which is mixed with a slurry of anti-CD15 and CD45-functionalized superparamagnetic particles (21), and incubated at room temperature for 10 min. After washing twice with PBS/1% BSA, the WBCs are ready for downstream applications.
Figure 16:
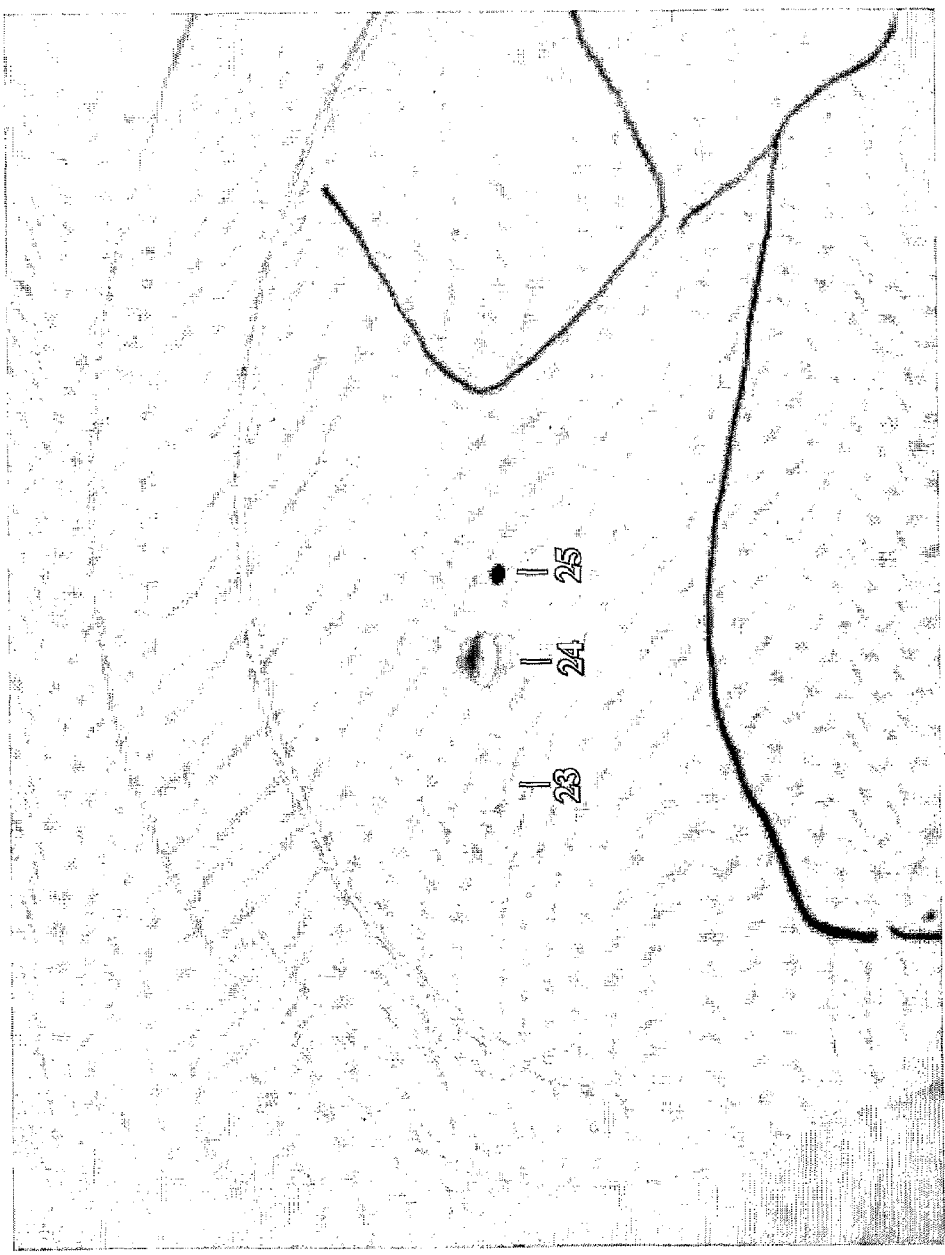
FIG. 16 shows the colourless solution of a droplet (23) containing the substrate solution A (3,3',5,5'-tetramethylbenzidine (TMB)) and B (hydrogen peroxide) turning dark (bluish/greenish, 24) after reacting with the GtxMs IgG FITC/RbtxGt IgG Fc HRP-coated superparamagnetic particles. To stop the reaction, the superparamagnetic particles (25) are removed from the reaction mixture.

FIGS. 7, 16 and 18 depict illustrative examples of fluid droplets, as used in the present invention, on a surface. The surface may before, during or after dispensing a fluid droplet thereon have any orientation relative to the ground. In embodiments where an essentially flat surface is provided and the fluid droplet is handled in a gas such as air, it may for convenience be desired to dispose the fluid droplet on top of the respective surface. Likewise, in such a case it may be desired to maintain the respective surface in an essentially horizontal position in order to assist controlling the position of the fluid droplet, especially where it is desired to position the fluid droplet my means of a magnetic field and thereafter to terminate the magnetic field. In such a case the fluid droplet is typically handled below or above the respective surface as depicted in FIG. 3A and FIG. 3B. In embodiments where a concave or convex surface is provided and the fluid droplet is handled in a gas such as air, it may for instance for convenience be desired to dispose the fluid droplet at a top or bottom position of a dent, relative to the direction of action of gravitation.

Since the method of the present invention typically does not require any further mechanical parts, it relies on a microfluidic system that is robust. The method of the invention typically does neither require valves, so that no dead volume occurs. Accordingly the method of the present invention is well suited for processing sample volumes in the nanoliter scale and below (supra) without any material loss.

Typically the method of the invention involves controlling the position of the fluid droplet, in particular relative to the at least one surface. This position may for instance be controlled by geometrical means, such as a concave surface (cf. FIG. 1E). Another means of controlling the position of the fluid droplet includes mechanical force. Such mechanical force can for instance be applied by contacting the fluid droplet with a further surface such as for instance the surface of a pipette tip. A further means of controlling the position of the fluid droplet includes the application of acoustic waves as disclosed by Guttenberg, Z. et al., Lab on a Chip (2005) 5, 308-317. Yet another means of controlling the position of the fluid droplet includes the application of a thermal gradient, e.g. of the at least one surface. A respective thermal gradient may for instance be obtained by means of an IR-laser.

In some embodiments the method of the invention controlling the position of said fluid droplet relative to the at least one surface further includes exposing the fluid droplet to a magnetic or an electromagnetic field. This exerts a force on the magnetic particles, such that the droplet as a whole is forced to follow any movement of the magnetic particles. Thereby the position of the fluid droplet can be controlled. In some embodiments a constant magnetic or electromagnetic field is applied, while in other embodiments the magnetic or electromagnetic field is altered during the method of the invention. In some embodiments controlling the position of the fluid droplet includes moving the surface, for instance under a constant magnetic or electromagnetic field. As a consequence the position of the fluid droplet relative to the surface can be altered. In some embodiments several means of controlling the position of a fluid droplet may be combined (cf. also below for further examples). In some embodiments the process is only performed once the fluid droplet has been positioned by means of the magnetic or electromagnetic field. In one of these embodiments, the magnetic or electromagnetic field is terminated after the fluid droplet has been placed in a desired position. As an illustrative example, a region of the at least one surface may be exposed to a condition such as an altered temperature, an (altered) magnetic field, an (altered) electrical field (including an electrostatic field), an (altered) electromagnetic field, an altered pressure, an (altered) wavelength, an (altered) frequency, an (altered) amplitude, an (altered) chemical concentration, and an (altered) chemical composition (such as a gas flow). In such a case controlling the position of the fluid droplet may include moving the fluid droplet into the region of the at least one surface that is being exposed to this condition.

In some embodiments of the method of the invention, exposing the droplet to an electric/magnetic field includes repelling the droplet. In some of these and in other embodiments exposing the droplet to an electric/magnetic field includes attracting the droplet. Attracting or repelling the droplet by means of a magnetic or an electric field may for instance be achieved by means of a bar magnet, an electromagnet, an array of bar magnets or electromagnets, or any combination thereof. A respective magnet may be moved in order to move one or more fluid droplets. The attractive or repelling forces of one or more magnets of an array may also be modified in order to control the position of a fluid droplet.

In some embodiments where at least two surfaces as defined above are provided, the fluid droplet may be transferred from one surface to another and be moved between them. In such embodiments controlling the position of the fluid droplet may include moving the fluid droplet between two surfaces by means of a magnetic or an electromagnetic field.

The method of the invention further includes performing a process on the biological and/or chemical sample in the fluid droplet. Any process may be performed that can be performed in a fluid droplet. Examples of processes that may be performed include, but are not limited to, a physical detection of target matter suspected or known to be included in the sample, a chemical reaction, a cell lysis, an extraction of a molecule from an organism or a part of an organism, a release of a molecule from an organism, and any combination thereof. Examples of a physical detection include, but are not limited to, a spectroscopic, a photochemical, a photometric, a fluorometric, a radiological, an acoustical, an electrochemical, a colourimetrical, a diffractional, an interferometrical, an elipsometrical, and a thermodynamic detection and include for instance the use of photoactive, fluorescent, radioactive or enzymatic labels. Two illustrative examples of a spectroscopic method are Raman microscopy and coherent anti-Stokes Raman scattering (CARS) microscopy. The latter technique is for example suitable for selective imaging of specific molecules of interest. Examples of a chemical reaction include, but are not limited to, a chemical synthesis, a chemical degradation, an enzymatic synthesis, an enzymatic degradation, a chemical modification, an enzymatic modification, an interaction with a binding molecule, and any combination thereof. Examples of an enzymatic synthesis include, but are not limited to a protein synthesis, a nucleic acid synthesis, a peptide synthesis, a synthesis of a pharmaceutical compound, and any combination thereof. The method of the invention is for example compatible with any biochemical transformation or assay format, e.g. the yeast-two-hybrid system, small interfering RNA (siRNA), transfection, ligation, etc.

Figure 13:
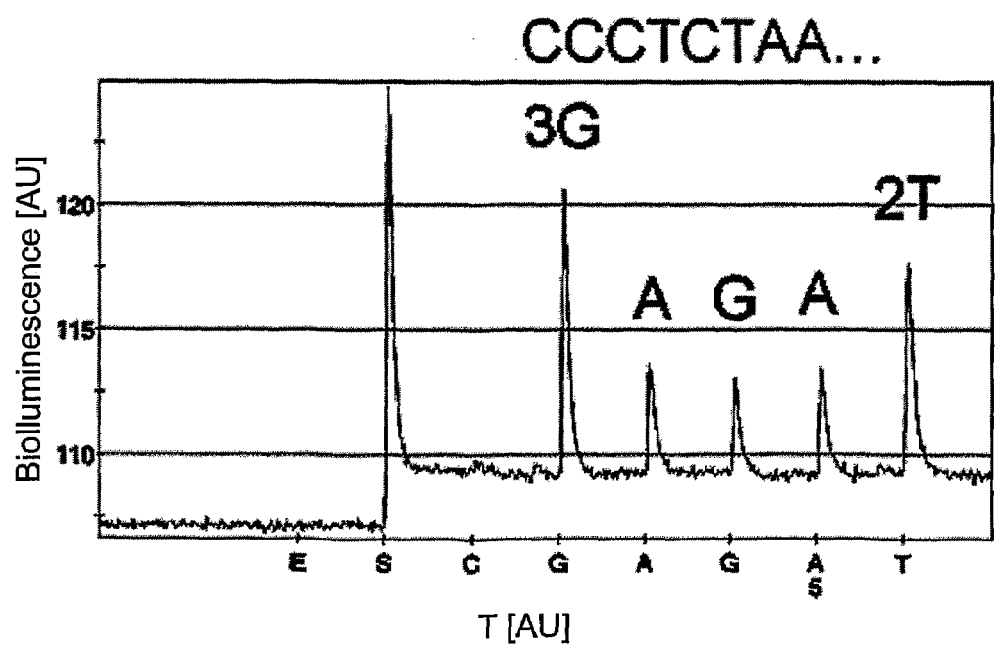
FIG. 13 depicts a pyrogram analysis obtained by fluid-phase pyrosequencing of the PCR product ($c_{dsDNA}$=20.5 ng/µl).

Performing a process may include an exposure to energy, for instance for a process to be initiated or catalyzed. Examples of energy that may be applied, include, but are not limited to, infrared radiation, microwave radiation, or photolytic energy. As an illustrative example, the surface together with a fluid droplet may be placed biochip on a thin film cooler/heater. Accordingly, chemical synthesis driven by elevated temperatures or requiring reduced temperatures may for instance be performed by adjusting the temperature of the environment of the droplet respectively. As another example, temperature-controlled biochemical reactions between 4 and 100° C. can be performed. Thus, temperature-sensitive biological samples may for instance be stored. Further examples include, but are not limited to, cell isolation (cf. FIG. 9), cell incubation, cell lysis (FIG. 6), reverse transcription, polymerase chain reaction (FIG. 10, 12), and pyrosequencing (FIG. 13). Pyrosequencing is a real-time nucleic acid sequencing technique, which is based on the detection of released pyrophosphate during the nucleic acid polymerization reaction (for an overview cf. e.g. Ronaghi, M, Genome Research (2001), 11, 3-11). Furthermore, the implementation of diverse optical detection systems, e.g. photodiodes (PD), photomultipliers (PMT), photon counting modules (PCM), spectrometers, and charge-coupled devices (CCDs) allows monitoring these biochemical reactions in parallel and real-time.

As an illustrative example, a pathogen, a bacterium, a virus, or a DNA sequence may be detected using the present invention for identifying a disease state. Diseases which can be detected include, but are not limited to, communicable diseases such as Severe Acute Respiratory Syndrome (SARS), Hepatitis A, B and C, HIV/AIDS, Dengue, swine fever, mouth-and-foot-disease, avian flu, anthrax, *salmonella*, malaria, polio, tuberculosis and influenza; congenital conditions that can be detected pre-natally (e.g. via the detection of chromosomal abnormalities) such as sickle cell anaemia, heart malformations such as atrial septal defect, supravalvular aortic stenosis, cardiomyopathy, Down's syndrome, clubfoot, polydactyl), syndactyl), atropic fingers, lobster claw hands and feet, etc. The present method is also suitable for the detection and screening for cancer, for identifying the pedigree of an animal, e.g. by means of a DNA-tag, or the detection and analysis of substances in blood, e.g. doping.

In other embodiments the method of the present invention may be employed for the detection, reaction (including a binding reaction to a biological cell or a part thereof), synthesis, or any combination thereof, of one or more pharmaceutical compounds, such as drugs. A synthesis of a compound, such as a pharmaceutical compound, may for example be performed as a solid-phase reaction on derivatised beads. Pharmaceutical compounds may for example be used in form of a library. Examples of such libraries are collections of various small organic molecules, chemically synthesized as model compounds, or nucleic acid molecules containing a large number of sequence variants. As an example, each compound of such a library may be disposed into one droplet. Such droplets may be provided in an automated way by commercially available machines, which are well known to those skilled in the art. The method of the invention may for instance be used for drug screening or for determining the presence of a drug in a urine or blood sample.

As a further example, a cell culture media may be suspected to be contaminated (supra). In this case it may be desired to identify the type of contaminant and to use the device of the invention for this purpose. The magnetically attractable matter may in such embodiments for instance be magnetically attractable particles carrying a ligand with an affinity to the contaminant or with an affinity to other matter that has an affinity to the contaminant.

In embodiments where it is desired to remove matter, such as by-products or undesired matter of the sample, the process may be a washing process or a process including a washing step. It may also include splitting the fluid droplet into at least two daughter fluid droplets. As an illustrative example, a nucleic acid may be extracted from a cell and be bound by a ligand attached to magnetic particles, while cell debris and reagents are to be discarded. FIG. 4A illustrates an example of a washing step of a fluid droplet using a further, additional fluid droplet. This further fluid droplet may also include two or more fluid phases. It may be provided on the same surface as the fluid droplet that includes two phases, magnetic matter and the sample, or it may be provided on another surface (FIG. 4B). It is moved toward the fluid droplet that includes two phases, magnetic matter and the sample (FIG. 4A(1)). The arrow in FIG. 4A indicates the current position of a permanent magnet. The two fluid droplets merge (FIG. 4A(2)) and form one larger fluid droplet (FIG. 4A(3)). To ensure a complete mixing and washing a weak magnetic force may be applied that is sufficient to for instance lift the magnetic particles within the droplet without raising the entire fluid droplet. By further moving the magnetic particles to one side (FIG. 4A(4)) a splitting of the droplet is initiated (FIG. 4A(5)). The ratio of magnetic particles/outer phase, the volume ratio of interacting fluid droplets, their biochemical composition, the surface morphology, the surface chemistry, and the strength of the (electro)magnetic field gradient dictate whether the corresponding fluid droplets move, merge, are 'washed' or split. During these manipulations the dead volume is zero, i.e. no material is lost even if nanoliter volumes are processed. Where desired, further functional units may easily be implemented in the method of the invention, e.g. piezoelectric-based actuators to assist or achieve mixing.

The inner phase of the droplet may be washed or exchanged with any fluid (see e.g. FIG. 18), for instance a solvent, an acid or a base, as long as the fluid allows for (a) the inner phase to remain essentially intact and (b) the magnetic particles to remain attractable to a magnet. In embodiments where the outer phase forms a film surrounding the inner phase (supra), it may furthermore be desired to keep the outer phase intact as a film. In embodiments where a ligand attached to magnetic particles is used to bind target matter, it may furthermore be desired that such a fluid allows for the ligand to remain intact and to bind the desired target matter. At any point in time before, during or after performing a process, a mixing of the fluid droplet may be carried out, for instance by exposing the fluid droplet to ultrasound. Since the droplet is based on a self-organising system, such mixing does not affect the integrity of the droplet, but rather assists in achieving an equal distribution of matter within a phase within the droplet.

The possibility to perform transfers of matter such as washing allow for complex processes to be performed. Since desired target matter may be bound to ligands immobilized on magnetic particles, the possibility to add, remove or exchange fluid, e.g. liquid, enables the isolation of any matter, e.g. peptides, proteins, DNA, RNA, small organic molecules, metal ions, etc. (supra) at any desired stage or step, and complex biochemical transformations can be carried out in sequence (FIG. 4). Furthermore the volume of the fluid droplet can be changed by several orders of magnitude. Accordingly the method of the present invention provides an interface between the macroscopic and microscopic world without any break in technology.

Where desired, the concentration of target matter in a sample may be increased by volume reduction according to techniques well known in the art such as gel-filtration, ultrafiltration or dialysis. A low volume as used in the method of the present invention, in particular in combination with a high concentration of target matter, makes biosensing of biomolecules in low absolute numbers possible.

As a further illustrative, but not limiting example, the method of the present invention may be used to carry out a sandwich-type enzyme-linked immunosorbent (ELISA) assay. The uses and capabilities of this assay are well known to those skilled in the art. By combining several fluid droplets, wherein each droplet contains at least one or more of the requisite reagents for the binding, washing and detection steps, it is possible to assay for the presence of target matter in a sample. As described above, the capture reagent may be coupled to magnetic beads. In a specific embodiment, the capture reagent is an antibody targeted to an antigen of interest. More specifically, the antibody may be directed to an antigen present in a HIV virus and the sample blood or serum suspected to contain this HIV virus. Detection of an antigen can be monitored through calorimetric and or spectroscopic analysis. This can occur after elution of substrates captured onto the probe or within the device itself without recourse to an elution step.

Figure 6:
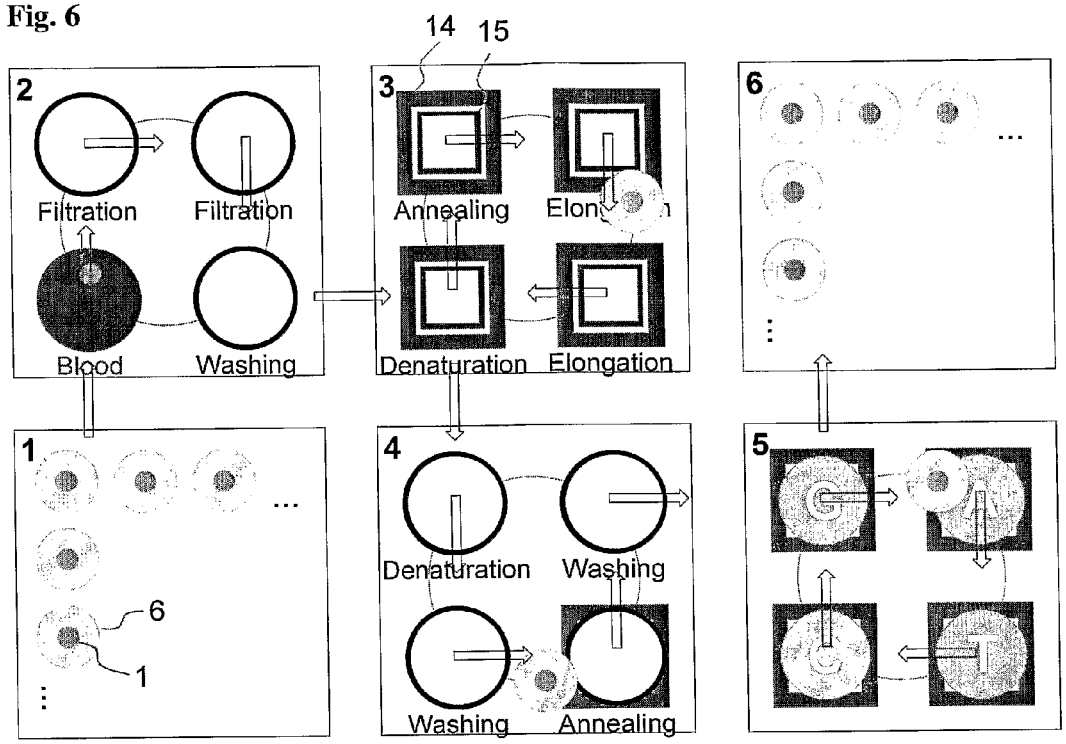
FIG. 6 depicts a genetic analysis of a blood droplet sample using the method of the invention. Leukocytes are bound to functionalized magnetically attractable particles (1) in droplets, isolated, washed, thermally lysed by means of thin film heaters (14) controlled by thin film sensors (15), and processed by reverse transcription (RT), followed by polymerase chain reaction (PCR) and pyrosequencing (PSQ). The arrows indicate the direction, in which the sample is moved.
Figure 8:
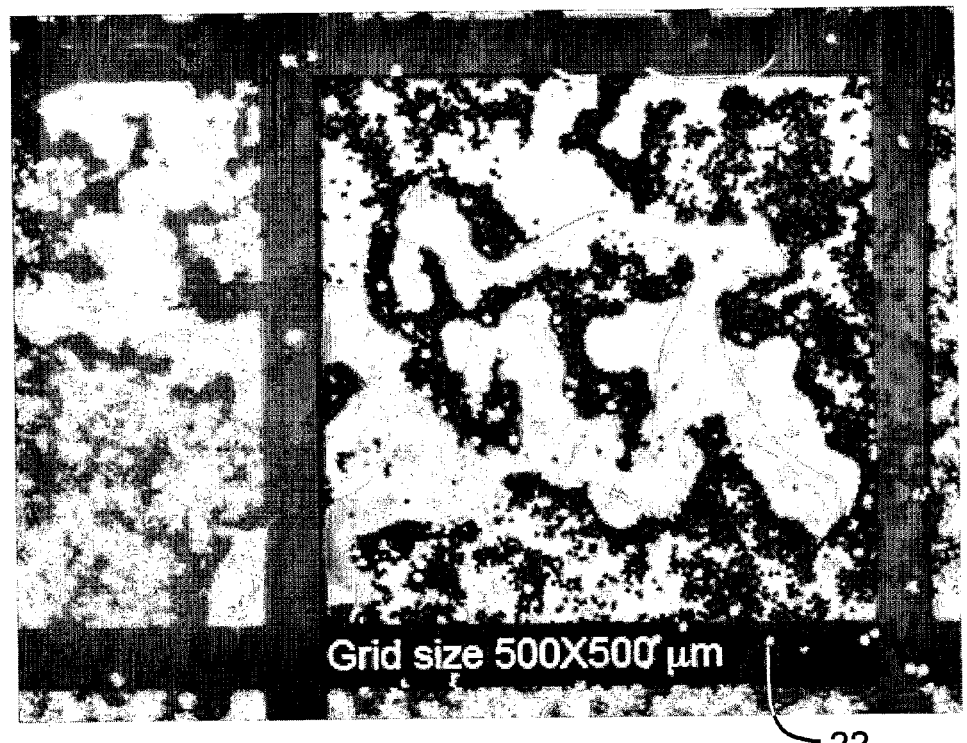
FIG. 8 depicts DAPI-stained white blood cells (22) immobilized on top of Dynabeads CD15 and CD 45 after washing.
Figure 11:
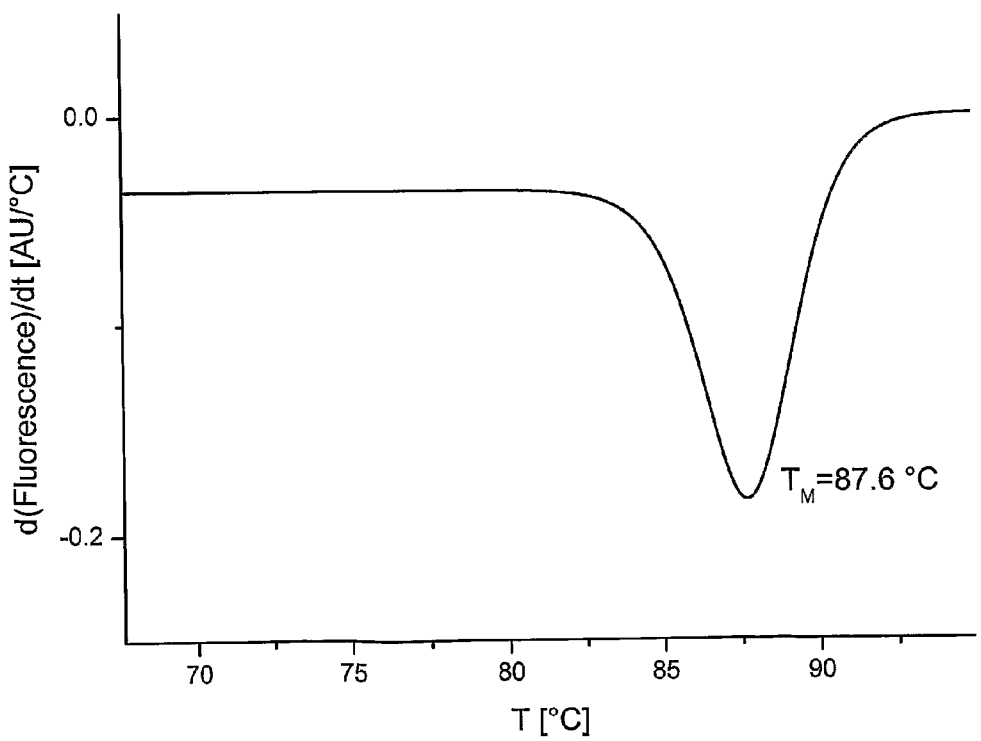
FIG. 11 depicts a melting curve analysis of the obtained PCR products. One peak ($T_M$=87.6° C., value obtained using an Opticon 2 thermocycler from MJ Research: $T_M$=84.6° C.) indicates one PCR product and little co-products.
Figure 17:
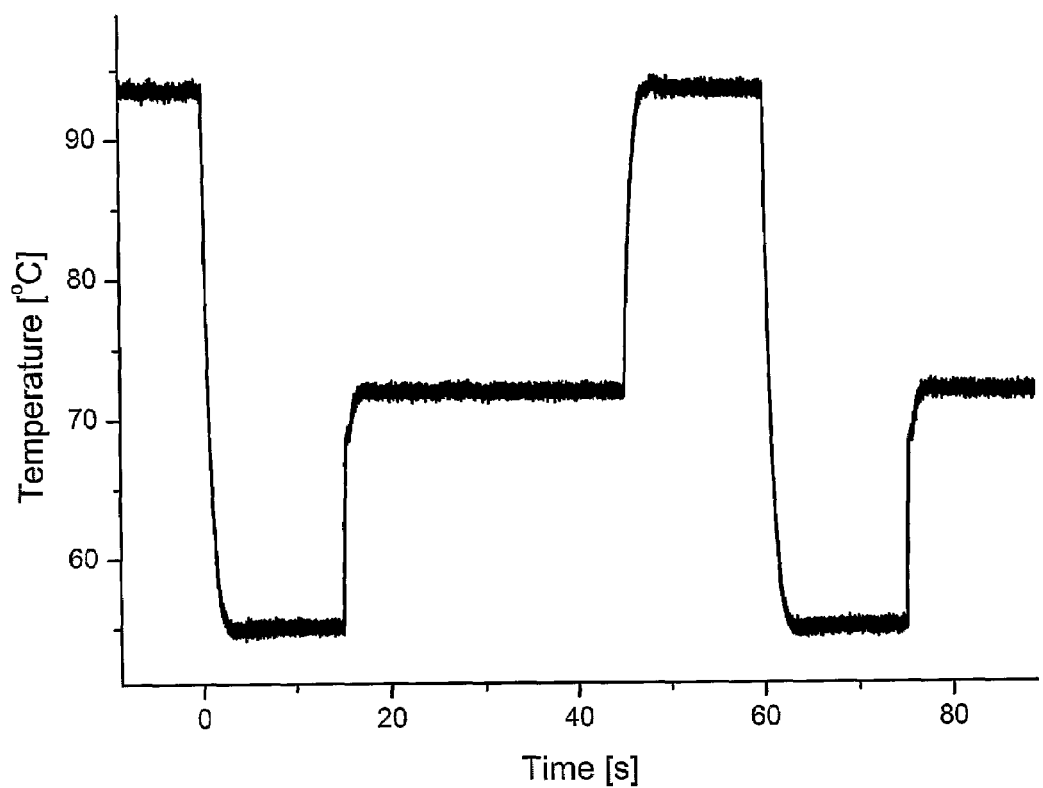
FIG. 17 depicts a temperature/time profile during PCR using the method of the present invention. Due to the low thermal mass of the chip, which is about 0.5 g, fast heating and cooling rates ($\pm 20$-50 K s$^{-1}$) can be carried out.
Figure 18A:
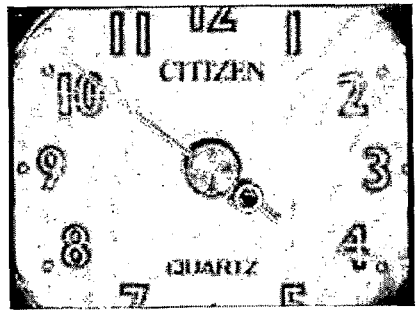
FIG. 18 depicts further examples of performing a process on the biological and/or chemical sample in a fluid droplet, which include moving the fluid droplet, merging the fluid droplet with a further fluid droplet, mixing the interior of the fluid droplet, washing the fluid droplet by means of another fluid droplet, and splitting the fluid droplet into daughter fluid droplets (cf. the Examples for details).
Figure 18B:
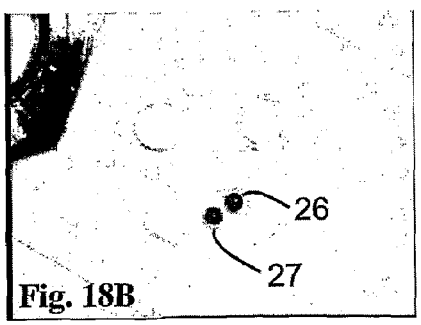
Figure 18C:
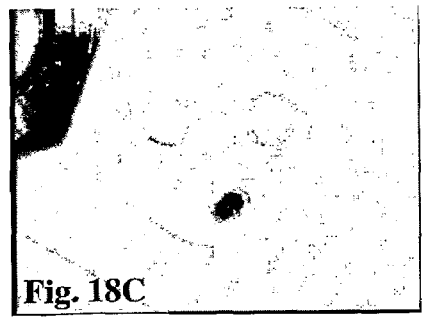
Figure 18D:
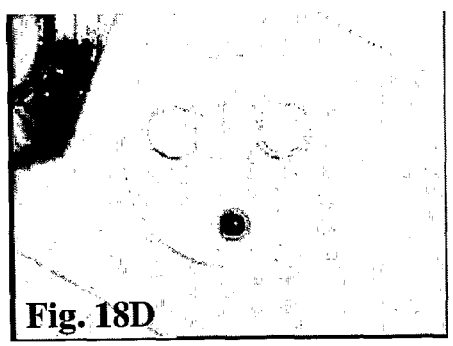
Figure 18E:
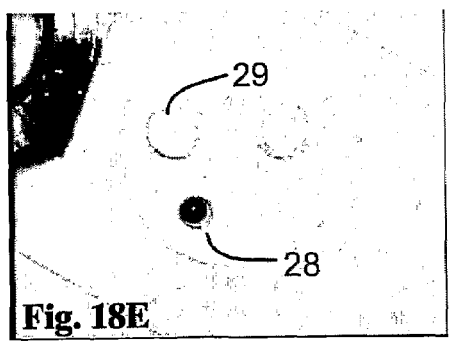
Figure 18F:
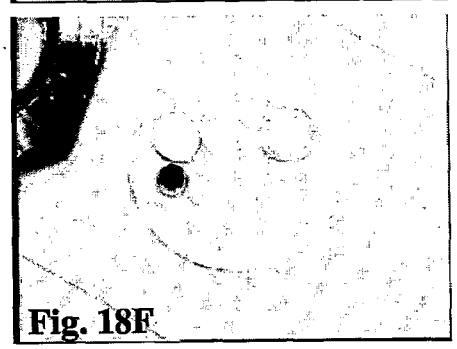
Figure 18G:
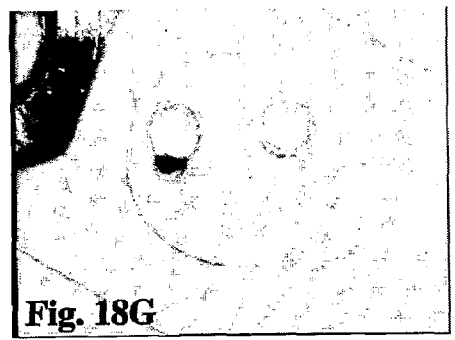
Figure 18H:
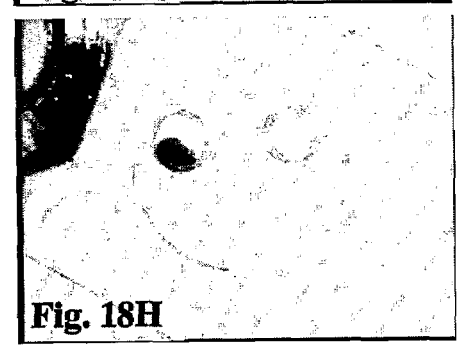
Figure 18I:
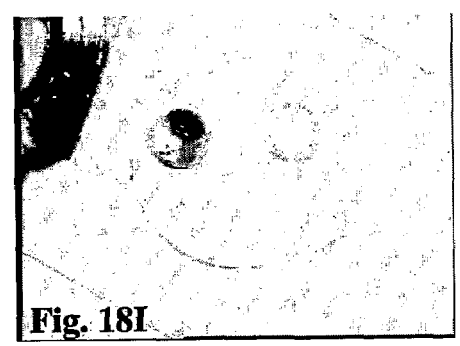
Figure 18J:
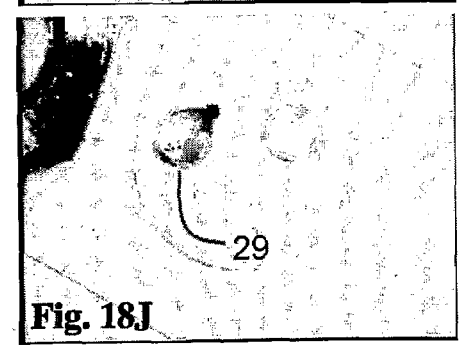
Figure 18K:
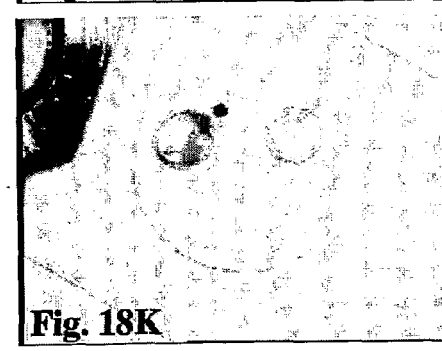
Figure 18L:
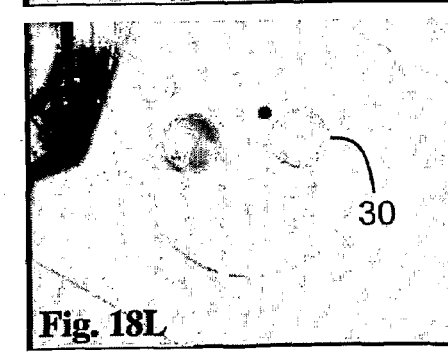
Figure 18M:
Figure 18N:
Figure 18O:
Figure 18P:
Figure 18Q:
Figure 18R:
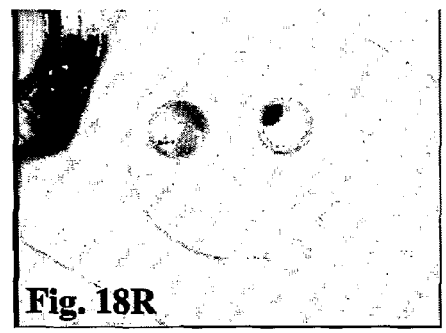
Figure 18S:
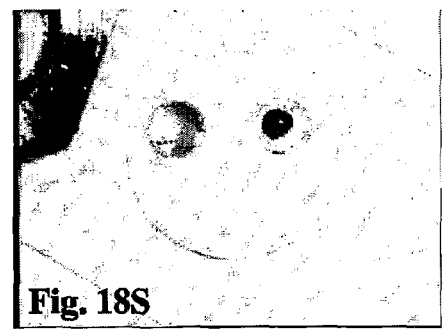
Figure 18T:
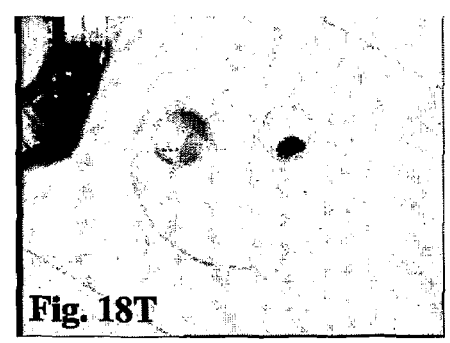
Figure 18U:
Figure 18V:
Figure 18W:

FIG. 6 illustrates the use of the method of the present invention for a polymerase chain reaction. Temperature control can be achieved by means of thin film heaters and temperature sensors. Module 1 represents a matrix of superparamagnetic particles, which are modified with ligands. These ligands are receptors directed against different cell surface markers. Any cell of interest may in this way be isolated from body fluids or tissue as described above. A drop of capillary whole human blood may be obtained by finger pricking with a lancet. This drop of blood is placed onto module 2. Leucocytes may then be isolated according to the binding of their cell surface markers to the ligand immobilized on the magnetic particles (cf. above, see also FIG. 5 and FIG. 7). FIG. 8 illustrates by way of magnification an example of leucocytes bound to ligands immobilized on magnetic particles. Leucocytes can be thermally lysed on one of the four thin film heaters of module 3. The polymerase chain reaction (PCR) is performed in a clock-wise manner by guiding the sample over three different temperature zones (cf. module 3 in FIG. 6). FIG. 17 depicts a temperature profile measured using the method of the present invention. FIG. 11 verifies that a PCR product obtained by the method of the present invention is of a quality that does not differ from a product obtained by conventional methods used in the art. Using time-space conversion makes multiplexing of samples possible. A biotinylated PCR product may be generated, which can be bound to streptavidin coated superparamagnetic particles. The amplification product can be chemically denatured on module 4 and annealed to a sequencing primer for pyrosequencing (PSQ), which may be carried out in a clock-wise manner on module 5 by moving the sample through four different VRCs containing the bases G, A, T and C. FIG. 13 shows an example of a respective analysis. Using time-space conversion makes multiplexing of samples possible. If desired, the samples can be stored on module 6 after pyrosequencing, again in a matrix-like format. Alternatively they can also be processed further.

A further example of performing a process on the biological and/or chemical sample in a fluid droplet is mixing the interior of the fluid droplet. The term "mixing" refers to passive interblending, i.e. by diffusion, to active mixing by means of e.g. applying external energy or forces, as well as to combinations thereof. Active mixing within a stationary or moving droplet may for example include agitating the superparamagnetic particles. Such agitation may be achieved for instance by altering a magnetic or electromagnetic field to which the droplet is exposed. It may also be achieved by altering the relative position of a droplet in a constant magnetic or electromagnetic field by moving the respective surface (supra). Yet another means of active mixing relies on ultrasound, which is illustrated in the appending Examples.

Figure 20A:
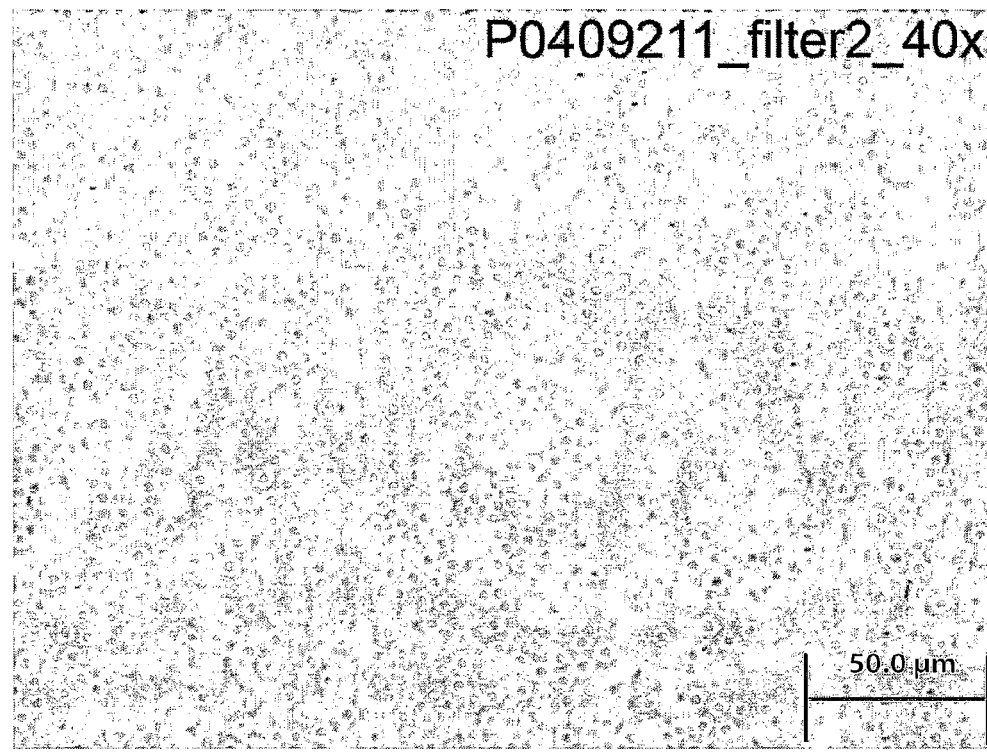
FIG. 20 shows the content of the washing solution obtained by an initial washing (A) and an additional washing solution obtained by a subsequent further washing (B) of the superparamagnetic particles-bound leucocytes. The additional washing solution hardly contains any erythrocytes. It illustrates the efficiency of washing with a single droplet to remove erythrocytes, which is about five orders of magnitude.
Figure 20B:
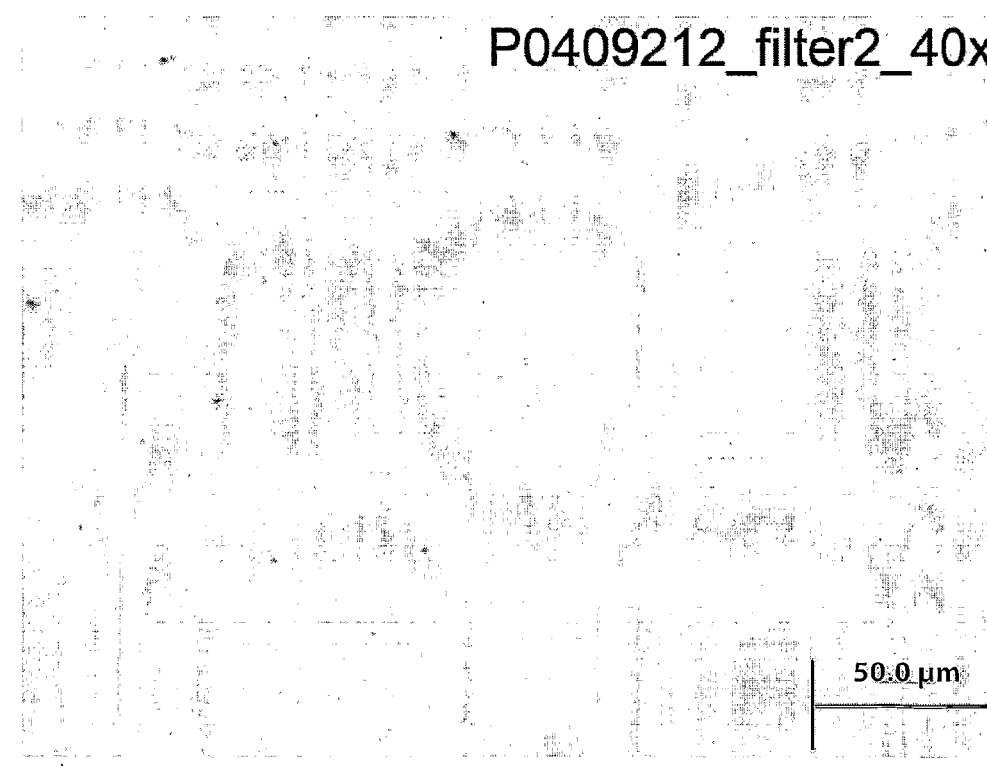

Yet another example of performing a process on the biological and/or chemical sample in a fluid droplet is filtering the fluid droplet through another fluid droplet, as illustrated in FIG. 18. Such a filtration is typically performed by means of moving a smaller droplet containing functionalized superparamagnetic particles with immobilized target matter through a bigger fluid droplet. In this way undesired components such as for example by-products, impurities, substrates, reagents, solvents or solvent components, salts, enzymes, waste, or buffers, can be diluted in the bigger droplet. Upon further movement of the magnetic particles out of the bigger droplet, essentially only the superparamagnetic particles including the immobilized target matter are being removed from the bigger droplet, while most of the undesired matter is being left behind. Due to the self-organizing nature of the system, the outer phase or a part thereof, is likewise removed from the larger droplet. In case of an outer phase in form of a film, a thin film of the outer phase may for example surround a small remaining amount of inner phase. In this way it is possible to substantially remove matter from the fluid droplet that is not immobilized by the magnetic beads. (cf. the Examples and FIG. 20). The underlying purification effect resembles the mechanism known from affinity chromatography, where target matter is held back by functionalized column material forming the stationary phase, and rinsed/washed several times with a washing solution, forming the mobile phase. In contrast to affinity chromatography, in the method of the present invention the washing solution is the stationary phase, while the functionalized material is the mobile phase. It should furthermore be noted that no dead volume occurs using the method of the present invention. Furthermore, in contrast to affinity chromatography, the method of the present invention allows for the elution of target matter in nanoliter volumes. This advantage is crucial in applications such as biosensing, when for example a high concentration of target matter is present in tiny volumes, or where fast kinetics are to be analysed.

Any part of the method of the present invention may be performed in a manual or in an automated way. Automated distribution of compounds, fluid and reagents, automated incubators and high-performance fluorescence readers, including plate readers, are already well established in the art. Typically, such equipment can directly be used with an apparatus of the present invention. Where required, adaptations of either such equipment or of the apparatus of the invention to a particular application are easily performed by a person skilled in the art.

Figure 10:
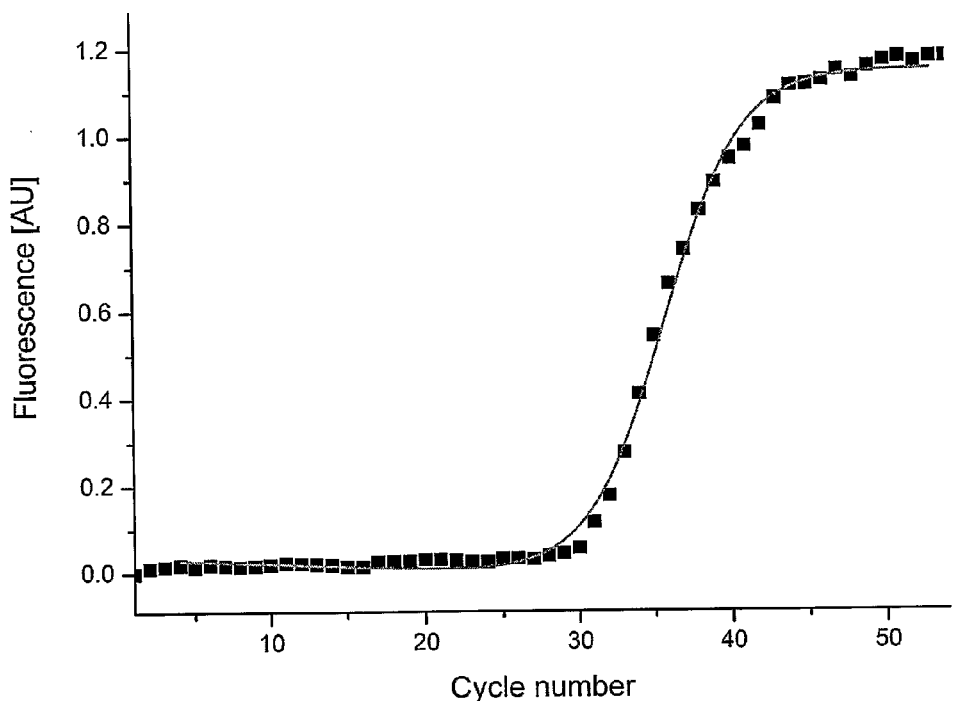
FIG. 10 depicts the amplification analysis of a RT-PCR in a droplet by real time detection.

Real time detection may provide an amplification plot depicting the fluorescence signal versus reaction time expressed as cycle numbers (see FIG. 16). An increase in fluorescence above the baseline indicates the detection of accumulating amplification product. Where a fixed fluorescence threshold is set above the baseline, the fluorescence signal thus passes this threshold at a certain time point. As time is expressed in terms of cycle numbers, a so called cycle threshold number (or value) or Ct value is obtained. The smaller this number, the further to the left is a respective fluorescence curve located in the amplification plot and the faster does amplification occur. The higher this number, the slower an amplification occurs and the less it becomes distinguishable from non-specific background reactions. An illustration of obtained fluorescence signals using the method of the present invention and is depicted in FIG. 10.

The method of the invention may be combined with such analytical and preparative methods, as for instance surface plasmon resonance, resonant mirror, reflectometric interference, giant magneto resistance, mass spectroscopy, ellipsometry, isoelectric focusing, chromatography methods, electrochromatographic, electrokinetic chromatography and electrophoretic methods. Examples of electrophoretic methods are for instance Free Flow Electrophoresis (FFE), pulsed field gel electrophoresis, Polyacrylamide gel electrophoresis (PAGE), Capillary Zone or Capillary Gel Electrophoresis. Surface immobilization of magnetic particles by charged proteins is for example known to shift their electrophoretic mobility up to several-fold. The combination with such methods may include a common step or a common device. As an example, a separation of proteins may be performed on a micro chip, for instance by isoelectric focussing. Subsequently a sample of the separation medium, e.g. a solution of ampholytes in water, known or suspected to contain matter, such as a protein, of interest may be used as e.g. the inner phase of a fluid droplet of the present invention. In case of the separation medium being a gel, the matter of interest may need to be extracted. The variety of suitable fluids for the inner and outer phase of the fluid droplet used in the present invention usually allows for the selection of a surface material that is well suited for usage as a surface for isoelectric focussing. As a consequence, a common surface may be shared for both methods where desired. Examples of a chromatography method include for instance gel filtration, size exclusion chromatography, ion exchange chromatography, affinity chromatography, hydrophobic interaction chromatography or hydrophobic charge induction chromatography. As an illustrative example, a respective analytical or preparative method may be performed before or after processing a sample using the method of the present invention.

In order that the invention may be readily understood and put into practical effect, particular embodiments will now be described by way of the following non-limiting examples.

EXAMPLES

Proplet Manipulation

Figure 19A:
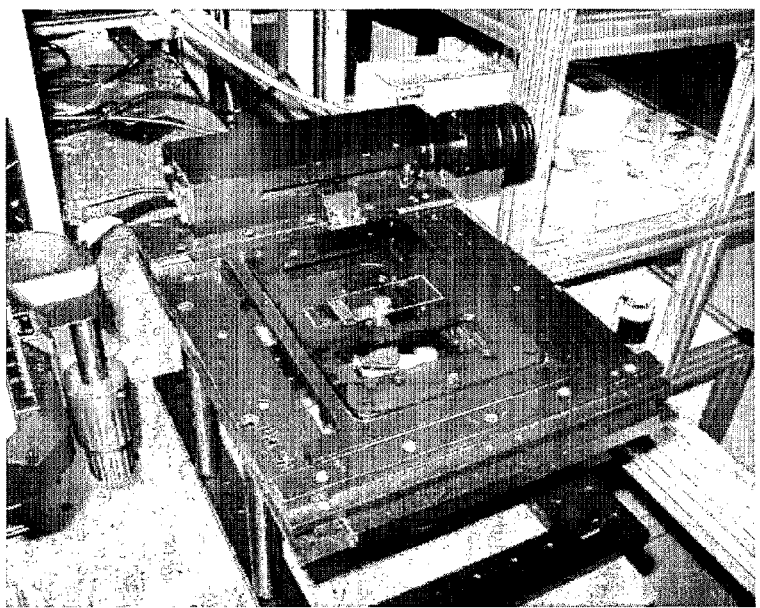
FIG. 19 shows an exemplary apparatus using an x, y-stage to manipulate the fluid droplets in the method of the present invention. A Teflon AF (amorphous fluoropolymer)-coated glass slide, fixed by tape, is moved relatively to a stationary permanent magnet (A), which is positioned on an x, y, z-stage (B, in detail).
Figure 19B:
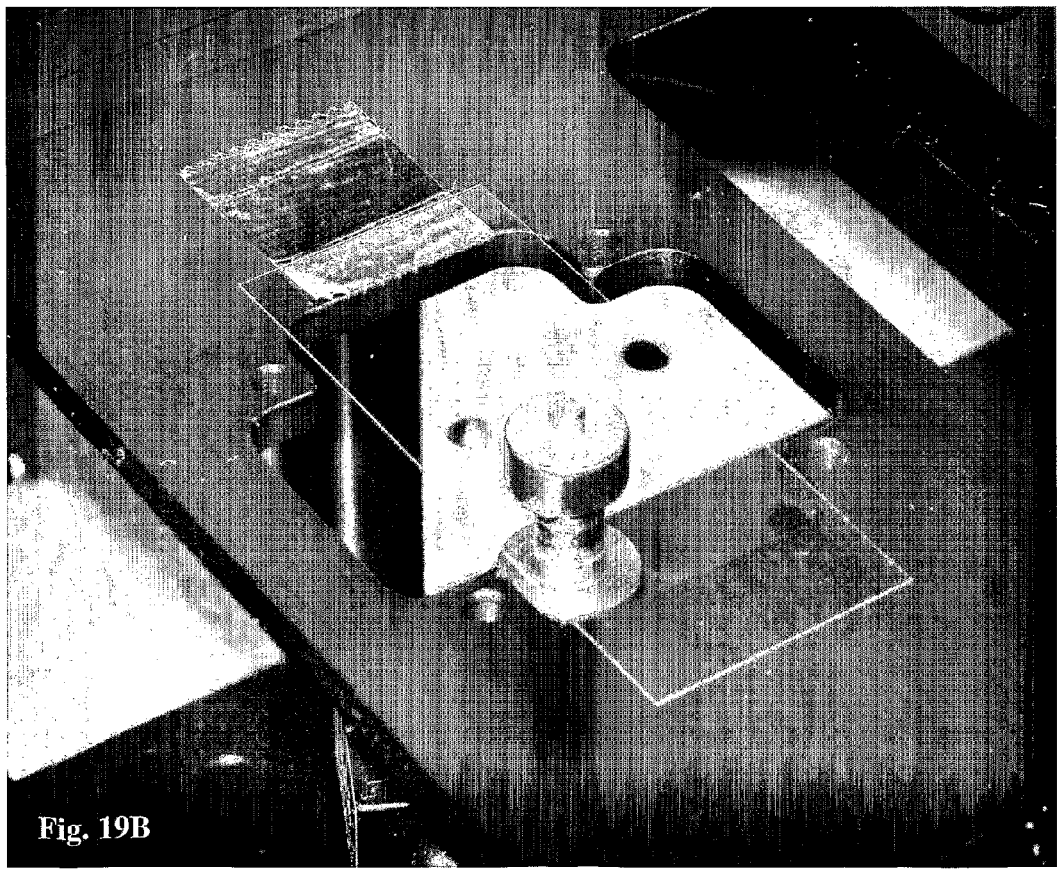

An in-house built array of electromagnets, a permanent M1219-X neodymium iron boron disc magnet (Assemtech), fixed to the handle of an analogue alarm-clock (Citizen) by double-sided tape (3M) (cf. FIG. 18a), or an A ProScanII-motorized stage system (Prior), which was moved relatively to a stationary permanent neodymium iron boron disc magnet (Farnell) and controlled by a joystick or LabVIEW 8-software (National Instruments) was used to manipulate fluid droplets containing superparamagnetic particles (cf. FIG. 19).

The fluid droplets contained a polar inner liquid phase and a non-polar outer liquid phase. The inner phase was aqueous and contained buffer, reagent(s) and superparamagnetic particles (cf. below). Ultrafiltrated mineral oil (Fluka) was used as immiscible liquid forming the outer phase in form of a thin film surrounding the inner phase. For applications at room temperature (rt), the volume ratio of the aqueous phase to the immiscible phase was 10:1, whereas for applications requiring elevated temperatures, e.g. pyrosequencing (PSQ), reverse transcription (RT), cell lysis, and polymerase chain reaction (PCR), it was 1:5.

The microfluidic manipulations included merging, mixing, washing/filtering, and splitting of droplets. Mixing within the droplet was achieved either by means of agitation of the superparamagnetic particles by altering the magnetic/electromagnetic field or by acoustic cavitation/streaming by ultrasound. In some cases both mixing techniques were combined.

To generate ultrasound, a 33250A 80 MHz function/arbitrary waveform generator (Agilent), equipped with an in-house built amplifier, and a lead zirconium titanate (PZT) disc (Phillips), glued to the substrate by an epoxy adhesive (Alteco), were used. Depending on the experiment, different waveforms in the kHz-range provided fast and efficient mixing. Except for the PCR solution, all droplets, i.e. blood, functionalized superparamagnetic particles, mineral oil, capping solutions, washing solutions, substrates, etc., were disposed onto the surface at the beginning of the experiment and the droplet containing the superparamagnetic particles was successively merged, mixed, washed/filtered, and split with these droplets.

FIG. 18 shows moving, merging, washing/filtering, and splitting for the following example of the isolation of white blood cells from fresh, capillary whole human blood using functionalized superparamagnetic particles (see below). Since white blood cells express CD15 and CD45 antigens (cell surface markers) on their cell membrane, they can be selectively removed by immunoreaction with anti-CD15 and anti-CD45 antibody-coated superparamagnetic particles. FIG. 18A: a permanent M1219-1 neodymium iron boron disc magnet (Assemtech), fixed on the handle of an analog clock (Citizen) by double-sided tape (3M), is used to move, merge, wash/filter, and split droplet(s) containing functionalized superparamagnetic particles (1), which are placed on top of a Teflon AF (DuPont)-coated glass slide (24×60 mm, thickness 180 µm, vfm CoverSlips, CellPath) above the magnet; for a better visibility in the following figures, a white paper is placed between the clock and the glass substrate. FIG. 18B: A droplet containing 100 nl of Dynabeads® CD15 and CD45 (Dynal Biotech) (26) is moved towards a droplet containing 100 nl fresh, capillary whole human blood (27), and merged (FIG. 18C, 18D). After merging of the two droplets, the combined droplet (28) is moved towards a droplet containing 10 µl of washing solution (0.01M PBS/0.1% BSA), (29) (FIG. 18E, FIG. 18F); during this incubation step, the white blood cells are immobilized on top of the functionalized particles, whereby the agitation of the moving superparamagnetic particles supports active mixing. In addition, acoustic streaming by ultrasound can be used to shorten the incubation time for this purpose. It should be noted that it is for a number of applications desirable to avoid acoustic cavitation at higher amplitudes, as this mode leads to the rupture/lysis of white blood cells. After merging (FIG. 18G), the immobilized white blood cells are washed/filtered. The term 'washing'/'filtering' refers to moving the functionalized superparamagnetic particles with immobilized white blood cells through a bigger droplet containing the washing solution (FIG. 18H, FIG. 18I). Upon doing so only the superparamagnetic particles including the immobilized white blood cells, together with a thin film of immiscible liquid of the outer phase by self-organization, leave (FIG. 18J) the bigger droplet. All other matter that is included in the bigger droplet, such as impurities, e.g. red blood cells, buffer, salts, EDTA (serving as anti-coagulant), heparin, RNases, DNases, etc. remain in the bigger droplet. The presence of red blood cells turns the washing solution red in color (cf. the dark stain of the remaining droplet). At the same time impurities, eventually part of the slurry of functionalized superparamagnetic particles with immobilized white blood cells, leaving the bigger droplet are being diluted. Thereby, the dilution factor is dependent on the volume ratio of the interacting droplets: if for instance a droplet of 0.1 µl of functionalized superparamagnetic particles with immobilized white blood cells is washed three times by 10 µl of washing solution, the remaining impurities within the slurry are diluted one million-fold [$(1:100)^3$]). Thereafter, the functionalized superparamagnetic particles with immobilized white blood cells leave the washing solution (29) (FIG. 18J) and are moved towards a second washing solution (30) (FIG. 18K, FIG. 18L) for a second washing step. To enhance washing, the functionalized superparamagnetic particles with immobilized white are moved for and backwards several times within the washing solution (FIG. 18M-FIG. 18U), before they leave the washing solution (FIG. 18V, FIG. 18W). Finally, the purified white bloods cells are ready for downstream applications, e.g. RT-PCR. The filter-efficiency of one washing solution for removing red blood cells (the main component of blood, which interferes with downstream applications due to contamination with RNases and DNases), was estimated by counting the red blood cells using a Neubauer-hemacytometer (FIG. 20A, FIG. 20B) and is ~100 000-fold, i.e. the combination of two washing solutions of 10 µl each removes all red blood cells within a sample volume of up to 1 ml (absolute number of red blood cells in a 1 ml sample is $5\times10^9$).

Thermal Management

The temperature control module, fabricated in house, comprised platinum (Pt) thin film heaters and temperature sensors, and an application specific integrated circuit (ASIC) controller (cf. FIG. 17). Alternatively, PCR experiments (without optical detection) were carried out on a PCT-200® Peltier Thermal Cycler (MJ Research), equipped with a Slide Griddle™ adaptor (MJ Research). The set-up of the thermal management is similar to other devices used in the art, such as e.g. disclosed by Guttenberg, Z. et al. (supra). Commercially available custom-made PCR-chips including controller/software were found suitable for usage in the method of the present invention. In some tests PCR chips from Advalytix (Brunnthal, Germany, www.advalytix.com) and of the Institute for Physical High Technology e.V. (Jena, Germany) were used.

Optical Detection

Fluorescence was detected by an Axiotech vario fluorescence microscope (Zeiss), equipped with a X-Cite 120 fluorescence illumination system (EXFO Life Sciences), a HE 38 FITC filter set (Zeiss), a 5784-20 photomultiplier tube (Hamamatsu) and recorded by a TDS50054B digital phosphor oscilloscope (Tektronix) according to the manufacturer's instructions.

For bioluminescence detection, a H7421-40 photon counting module (Hamamatsu) was used instead.

Surface Modification

Hydrophobic as well as oleophobic surfaces were obtained by either chemical vapour deposition (CVD) of glass (Schott) or silicon (Silicon Sense) substrates with (heptadecafluoro-1,1,2,2-tetrahydrodecyl)triethoxysilane (Gelest) in a 15E oven (Yield Engineering Systems) at 150° C. and 0.5 mbar for 2 h, or spin-coating of glass, silicon or polymeric substrates (General Electric) with a 1% solution of Teflon AF (DuPont) in FC-70 (3M). Static contact angles with water and mineral oil (Fluka), measured by an OCA 30 contact angle measuring device (DataPysiscs), were >110 and >70°, respectively.

The following sequence, isolation of white blood cells (WBCs) from whole human blood, cell lysis of WBCs, PCR, and PSQ was performed successively, without any user interference (FIG. 6).

Isolation of White Blood Cells

A droplet containing 0.1 µl of a 1:1 suspension of 200 µg µl$^{-1}$ of Dynabeads CD15 and CD45 (Dynal Biotech) in 0.01 M phosphate buffered saline PBS (Sigma-Aldrich)/1% bovine serum albumin (BSA) (Roth) was merged with a droplet containing 15 µl of fresh capillary whole human blood, mixed, incubated at rt for 10 min, and washed successively in two droplets containing 10 µl 0.01 M PBS/1% BSA and one droplet containing 10 µl of the PCR mixture (FIG. 7). The white bloods cells (WBCs), attached onto the superparamagnetic particles, and were now ready for the cell lysis.

Figure 9:
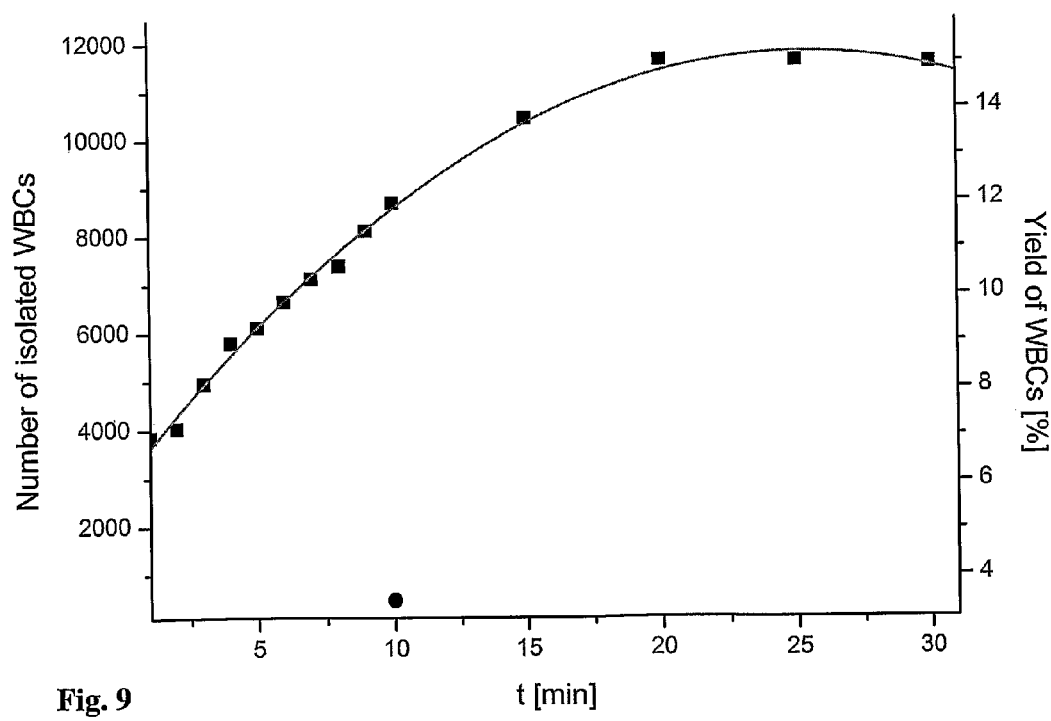
FIG. 9 depicts absolute numbers (left ordinate axis) and relative yield (right ordinate axis) of leukocytes isolated from a drop of human blood (■), and 100 nl (●); for 100 nl blood, the relative yield of isolated leukocytes is 85% after 10 min.

To count the number of isolated WBCs, the droplet containing the superparamagnetic particles was merged (cf. below) with a droplet containing 10 µl of a 4% solution of paraformaldehyde (Roth) in 0.01 M PBS/1% BSA, mixed (cf. below), and incubated at 4° C. for 30 min, and washed successively in three droplets containing 10 µl 0.01 M PBS/1% BSA. After fixation of the WBCs, the droplet containing the superparamagnetic particles was merged with a droplet containing 1 µl of VECTASHIELD® mounting medium with 4',6-diamidino-2-phenylindole (DAPI) (Vector) mixed, and incubated at 4° C. overnight. Finally, the DAPI-stained WBCs were covered with a high resolution-printed polymeric foil (Infinite Graphics) with a grid size of 500×500 µm, placed under a BX51 system microscope (Olympus), photographed with a DP70 digital camera (Olympus), converted into greyscale (FIG. 8) and counted software-assisted by MetaMorph_V6.1 (Molecular Devices) (FIG. 9).

Cell Lysis

After isolation of the WBCs, the droplet containing the superparamagnetic particles was merged with a droplet containing 1 µl of the PCR mixture, mixed and incubated at 95° C. for 5 min. After thermal lysis of the WBCs, the superparamagnetic particles were removed from the droplet containing the PCR mixture. The released genomic DNA was now ready for the PCR.

PCR

A housekeeping gene, glyceraldehyde-3-phosphate dehydrogenase (GAPDH) was used as the target, whereby the amplicon length was 208 bp (Maxim Biotech). Biotin-CTC ATT TCC TGG TAT GAC AAC GA (SEQ ID NO: 1) and GTC TAC ATG GCA ACT GTG AGG AG (Research Biolabs, SEQ ID NO: 2) were used as forward and reverse primers, respectively. The singleplex PCR mixture was prepared based on the Taq PCR Core Kit (QIAGEN) in a 50 µl stock solution and had the following composition: 23.0 µl diethyl pyrocarbonate (DEPC) treated H$_2$O (Invitrogen), 10.0 µl 5× Q-solution, 5.0 µl 5×PCR buffer, 5.0 µl 10% BSA, 1.0 µl 10 mM dNTPs, 0.5 µl 1:100 SYBR Green (Invitrogen), 2.50 µl 10 µM forward and reverse primer each, and 0.5 µl 5 u µl$^{-1}$ Taq DNA polymerase. For this particular PCR, ~1400 WBCs, isolated as described above, were used as the template.

Figure 12:
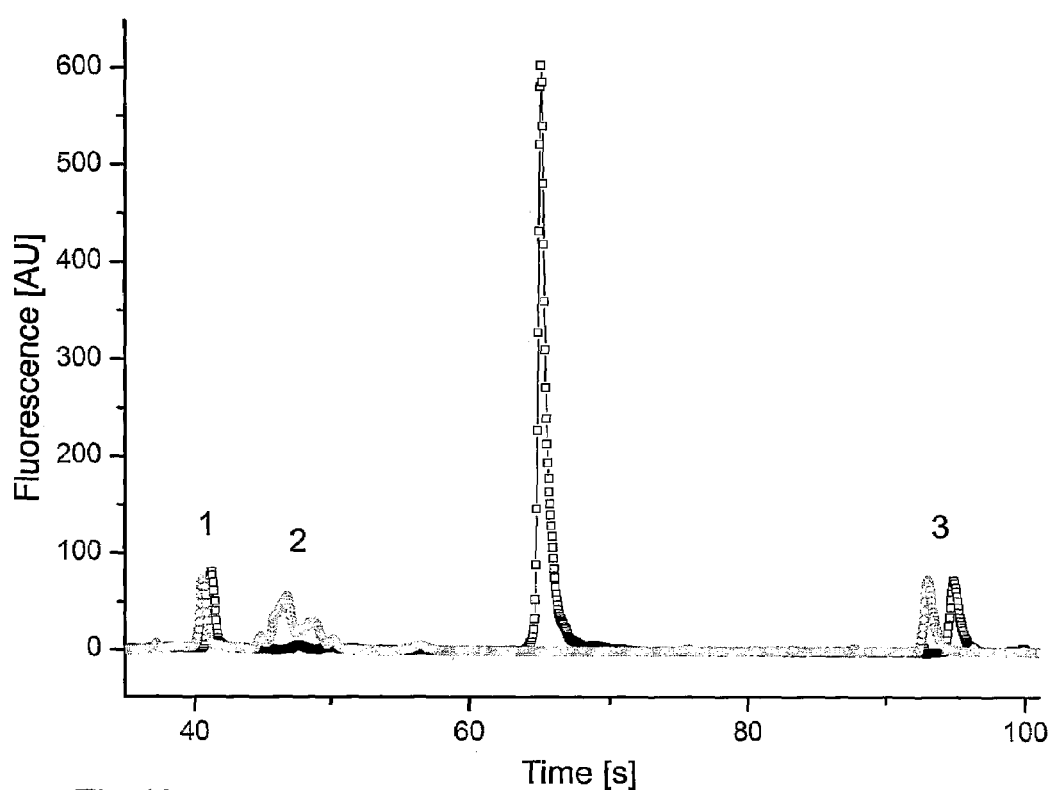
FIG. 12 depicts the verification of the identity of the cDNA fragment amplified (FIG. 10) by capillary electrophoresis. 100 nl CD45/15 with about 1400 white blood cells (■) or a negative (no template) control (NTC. ●, grey), 1 µl PCR mixture and 5 µl mineral oil were used, the sample resulting in a PCR product of 208 bp (yield 20.5 ng/µl). 1: marker of 15 bp, 2: primer dimer, 3: marker of 600 bp.

Thermocycling conditions were as follows: 45 cycles at 95° C. for 1 min, 58° C. for 1 min, 72° C. for 1 min, and 80° C. for 15 s. The mean value of the fluorescence intensity during this 80° C.-interval was extracted to follow the PCR in real-time (FIG. 10). For melting curve analysis, the sample was cooled down to 65° C. for 1 min, after which the temperature was continuously raised to 95° C. with a slope of 0.01 K s$^-$ (FIG. 11). Finally, the PCR products were analyzed by capillary electrophoresis using a Bioanalyzer 2100 (Agilent Technologies) (FIG. 12). After completion of the PCR, the biotinylated PCR product was ready for PSQ.

PSQ

For the PSQ, the 5×96 PSQ™ 96 MA Pyro Gold Reagent Kit including consumables (Biotage) was used. CAT GGC AAC TGT GAG GAG (SEQ ID NO: 3) served as sequencing primer. A droplet containing 1 µl of a suspension of 300 µg µl$^{-1}$ of Dynabeads® MyOne™ Streptavidin in 2× binding buffer was merged (supra) with the droplet containing the PCR mixture, mixed, and incubated at 65° C. for 15 min. After immobilization of the biotinylated PCR product, the droplet containing the superparamagnetic particles was merged with a droplet containing 10 µl of 1× denaturation solution, mixed, incubated at rt for 1 min, and washed successively in two droplets containing 10 µl of 1× washing buffer. Alternatively, the double stranded (ds) DNA could be denatured thermally at 95° C. for 1 min. After denaturation of the ds DNA, the droplet containing the superparamagnetic particles was merged with a droplet containing 1 µl of a solution of 0.3 µM sequencing primer in 1× annealing buffer, mixed, incubated at 80° C. for 2 min, and cooled down to rt. The single stranded (ss) DNA, attached onto superparamagnetic particles, was now ready for PSQ.

To verify the immobilization of ss DNA onto the superparamagnetic particles, the droplet containing the superparamagnetic particles was suspended in 50 µl 1× annealing buffer and sequenced in a commercial PSQ™ 96MA system (Biotage) (FIG. 13).

Figure 14:
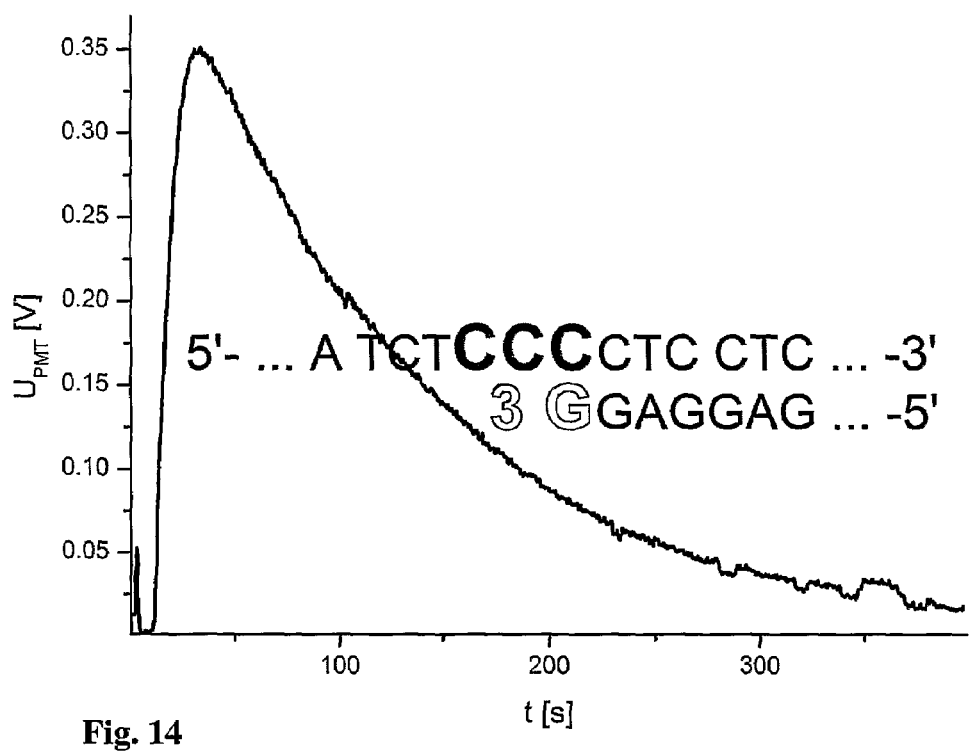
FIG. 14 depicts a pyrogram analysis of the first three base positions obtained by droplet-based pyrosequencing using the method of the invention.

Finally, the droplet containing the superparamagnetic particles was merged with a droplet containing 2.5 µl of a solution of dGTP, mixed, and then merged with droplet containing 10 µl of a 1:1 solution of enzyme and substrate mixture (FIG. 14).

Affinity Purification of a Protein

Green Fluorescent Protein

This example illustrates how a protein can be purified using the method of the present invention.

A fluid droplet containing 1 µl of an aqueous inner phase containing 50 mM Tris-HCl pH 7.7, 200 mM NaCl, 5 mM EDTA and Streptavidin-modified magnetic agarose beads (QIAGEN, equivalent to a 4% (w/v) suspension), and an outer phase of ultrafiltrated mineral oil (Fluka) can be prepared after washing the tagged agarose beads with 0.01 M phosphate-buffered saline (PBS). A droplet containing 1 µl of a crude bacterial lysate (*E. coli*) containing biotinylated recombinant green fluorescent protein (GFP) in above buffer (50 mM Tris-HCl pH 7.7, 200 mM NaCl, 5 mM EDTA) can be merged with the droplet containing the magnetic agarose beads. The obtained droplet can be incubated at room temperature for 45 min. Thereafter, the droplet can be washed successively in three droplets containing 10 µl of above buffer (50 mM Tris-HCl pH 7.7, 200 mM NaCl, 5 mM EDTA). Elution of the purified GFP in the obtained droplet of 1 µl can be performed by merging with a droplet of 25 µl containing 10 mM biotin in above buffer, and mixing by exposure to ultrasound, whereafter the magnetic agarose beads were removed. Quantification may be performed by any standard method such as the ratio of UV absorption at 280 and 260 nm according to Layne, by performing a colour reaction in a reference droplet, for example according to Bradford, separation by SDS-polyacrylamide-gel-electrophoresis and a subsequent stain, or by fluorescence detection using a reference solution of GFP of known concentration.

Enzyme-Linked Immunosorbent Assay (ELISA)

A droplet containing 1 µl of a suspension of carboxy-functionalized superparamagnetic particles in 0.1 M 2-morpholinoethanesulfonic acid (MES) (Lancaster) was merged (supra) with a droplet containing 10 µl of a 0.2 M solution of N-ethyl-N'-(3-dimethylaminopropyl)carbodiimide hydrochloride (Lancaster) and 0.02 M N-hydroxysuccinimide (NHS) (AlfaAesar) in 0.1 M MES, mixed, incubated at rt for 1 min, and washed in one droplet containing 10 µl 0.01 M phosphate buffered saline (PBS) (Sigma-Aldrich). After activation of the carboxy groups, the droplet containing the superparamagnetic particles was merged with a droplet containing 1 µl of a 1 µg µl$^{-1}$ solution of fluorescein (FITC)-labelled goat anti-mouse IgG (whole molecule) (GtxMs IgG FITC) (Sigma-Aldrich) in 0.01 M PBS, mixed, incubated at rt for 1 min, and washed in one droplet containing 10 µl 0.01 M PBS. After coupling of the GtxMs IgG FITC (FIG. 15), the droplet containing the superparamagnetic particles was merged with a droplet containing 10 µl 0.1 M 2-aminoethanol (Sigma-Aldrich), mixed, incubated at rt for 1 min, and washed successively in three droplets containing 10 µl 0.01 M PBS/1% BSA. After capping of the residual succinimide ester groups, the droplet containing the superparamagnetic particles was merged with a droplet containing 1 µl of a 1 µg µl$^{-1}$ solution of horseradish peroxidise (HRP)-labelled rabbit anti-goat IgG Fc (RbtxGt IgG Fc HRP) (Chemicon) in 0.01 M PBS/1% BSA, mixed, incubated at rt for 1 min, and washed successively in five droplets containing 10 µl 0.01 M PBS/1% BSA or 10 µl 0.01 M PBS/0.05% Tween 20 (Sigma-Aldrich). After immunoreacting of GtxMs IgG FITC and RbtxGt IgG Fc HRP, the droplet containing the superparamagnetic particles was merged with a droplet containing 10 µl of a 1:1 solution of peroxidase substrate solution A and B (Bethyl), mixed, incubated for 1-10 min, and split (cf. FIG. 16).

What is claimed is:

1. A method of processing a biological and/or chemical sample, comprising:
    providing a fluid droplet, said fluid droplet comprising an inner phase and an outer phase,
    wherein the outer phase is immiscible with the inner phase, and the outer phase is surrounding the inner phase as a film, and
    wherein the inner phase comprises said biological and/or chemical sample, and the inner phase is shielded from the environment by the outer phase, and
    wherein said fluid droplet comprises magnetically attractable matter;
    providing at least one surface, the surface being of such a texture and such a wettability for the fluid of said inner phase of the fluid droplet, that the fluid droplet remains intact upon being contacted therewith;

wherein the fluid of said inner phase of the fluid droplet is a non-polar liquid and said at least one surface is a polar surface, or wherein the inner phase of the fluid droplet is a polar liquid and the outer phase of the fluid droplet is a non-polar liquid;

disposing said fluid droplet onto said at least one surface;

exposing said fluid droplet to a magnetic or an electromagnetic field, thereby controlling the position of said fluid droplet relative to said at least one surface; and performing a process on the biological and/or chemical sample in said fluid droplet.

2. The method of claim 1, wherein the magnetically attractable matter is selected from the group consisting of at least one magnetically attractable particle, a magnetic fluid, an iron-rich bacterium, and a combination thereof.

3. The method of claim 1, wherein controlling the position of said fluid droplet relative to said at least one surface further comprises a member of the group consisting of moving the fluid droplet by altering said magnetic or electromagnetic field, moving said at least one surface, and a combination thereof.

4. The method of claim 3, wherein altering a magnetic field comprises altering the position of at least one magnet.

5. The method of claim 1, wherein the wettability of said at least one surface for the fluid of said inner phase of the fluid droplet is characterized by an advancing contact angle θ at the interface of a fluid droplet, which is made up of the fluid of the inner phase of said fluid droplet, with said at least one surface of about 50 degrees or higher.

6. The method of claim 1, wherein said at least one surface is selected from the group consisting of an essentially flat substrate, a concave substrate, a convex substrate, and any combination thereof.

7. The method of claim 1, wherein the inner phase of the fluid droplet directly contacts matter that is comprised in said surface.

8. The method of claim 1, wherein providing said fluid droplet comprises:

providing a first fluid, providing a second fluid that is immiscible with the first fluid, and dispensing a droplet of the first fluid onto the second fluid, thereby forming a fluid droplet comprising an inner phase and an outer phase, the first fluid forming the inner phase, surrounded by the second fluid forming the outer phase.

9. The method of claim 8, wherein said first fluid is provided first.

10. The method of claim 8, wherein providing said fluid droplet further comprises:

collecting said fluid droplet comprising an inner phase and an outer phase, or a part thereof, out of said second fluid that is forming the outer phase, thereby forming a fluid droplet comprising an outer phase surrounding the inner phase as a film.

11. The method of claim 1, wherein the inner phase of the fluid droplet is a polar liquid and the outer phase of the fluid droplet is a non-polar liquid, and wherein the inner phase of the fluid droplet is a hydrophilic liquid and the outer phase of the fluid droplet is a hydrophobic liquid.

12. The method of claim 1, wherein the inner phase of the fluid droplet is a polar liquid and the outer phase of the fluid droplet is a non-polar liquid, and wherein the fluid of the inner phase is selected from the group consisting of water, deuterium oxide, tritium oxide, an alcohol, an organic acid, an inorganic acid, an ester of an organic acid, an ester of an inorganic acid, an ether, an amine, an amide, a nitrile, a ketone, an ionic detergent, a non-ionic detergent, carbon dioxide, dimethyl sulfone, dimethyl sulfoxide, a thiol, a disulfide, and a polar ionic liquid.

13. The method of claim 1, wherein the inner phase of the fluid droplet is a polar liquid and the outer phase of the fluid droplet is a non-polar liquid, and wherein the fluid of the outer phase is selected from the group consisting of a mineral oil, a silicone oil, a natural oil, a perfluorinated carbon liquid, a partially halogenated carbon liquid, an alkane, an alkene, an alkine, an aromatic compound, carbon disulfide, and a non-polar ionic liquid.

14. The method of claim 2, wherein said at least one magnetically attractable particle is selected from the group consisting of a diamagnetic particle, a ferromagnetic particle, a paramagnetic particle, and a superparamagnetic particle.

15. The method of claim 2, wherein said at least one magnetically attractable particle comprises a ligand that is capable of binding target matter suspected to be comprised in said biological and/or chemical sample.

16. The method of claim 15, wherein said ligand is capable of selectively binding target matter suspected to be comprised in said biological and/or chemical sample.

17. The method of claim 15, wherein said ligand is immobilized on the surface of the at least one magnetically attractable particle.

18. The method of claim 17, wherein said ligand is selected from the group consisting of a crown ether, a peptide, an antibody, a mutein based on a polypeptide of the lipocalin family, a protein based on the ankyrin or crystalline scaffold, an avimer, a glubody, a lectin, a nucleic acid, protein A, protein G, an enzyme, a metal atom, a carbon nanotube, carbon nanofoam, a dye, streptavidin, amylose, maltose, cellulose, chitin, an extracellular matrix, glutathione, calmodulin, gelatine, polymyxin, heparin, NAD, NADP, lysine, arginine, benzamidine and an alumosilicate.

19. The method of claim 1, further comprising exposing a region of said at least one surface to a condition selected from the group consisting of an altered temperature, a magnetic field, an electrical field, an electromagnetic field, a pressure, a wavelength, a frequency, an amplitude, a chemical concentration and a chemical composition, and wherein controlling the position of said fluid droplet relative to said at least one surface comprises moving said fluid droplet into the region of said at least one surface that is being exposed to said condition.

20. The method of claim 1, further comprising providing at least two surfaces that are facing each other, the surfaces being of such a texture and such a wettability for the fluid of said inner phase of the fluid droplet, that the fluid droplet remains intact upon being contacted therewith.

21. The method of claim 20, wherein controlling the position of said fluid droplet comprises moving said fluid droplet between said at least two surfaces by means of said magnetic or electromagnetic field, and/or by moving at least one of the surfaces.

22. The method of claim 1, wherein performing a process on the biological and/or chemical sample comprises a step selected from the group consisting of merging said fluid droplet with a further fluid droplet, mixing the interior of the fluid droplet, filtering the fluid droplet through another fluid droplet, and splitting the fluid droplet into at least two daughter fluid droplets.

23. The method of claim 1, wherein the biological and/or chemical sample is exposed to a process selected from the group consisting of a physical detection of target matter suspected to be comprised in the sample, a chemical reaction, a biochemical reaction, a cell lysis, an extraction of a molecule from an organism or a part of an organism, and any combination thereof.

24. The method of claim 23, wherein the physical detection reaction is selected from the group consisting of a spectroscopic, a photochemical, a photometric, a fluorometric, a radiological, an electrical, an acoustical, an electrochemical, a colourimetrical, an interferometrical, a diffractional, and a thermodynamic detection.

25. The method of claim 23, wherein the chemical reaction is selected from the group consisting of a chemical synthesis, a chemical degradation, an enzymatic synthesis, an enzymatic degradation, a chemical modification, an enzymatic modification, an interaction with a binding molecule, and any combination thereof.

26. The method of claim 25, wherein the enzymatic synthesis is selected from the group consisting of a protein synthesis, a nucleic acid synthesis, a peptide synthesis, a synthesis of a pharmaceutical compound, and any combination thereof.

27. The method of claim 1, wherein the sample is selected from the group consisting of a soil sample, an air sample, an environmental sample, a cell culture sample, a bone marrow sample, a rainfall sample, a fallout sample, a space sample, an extraterrestrial sample, a sewage sample, a ground water sample, an abrasion sample, an archaeological sample, a food sample, a blood sample, a serum sample, a plasma sample, a urine sample, a stool sample, a semen sample, a lymphatic fluid sample, a cerebrospinal fluid sample, a naspharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a nail sample, a hair sample, a skin sample, a cancer sample, a tumour sample, a tissue sample, a cell sample, a cell lysate sample, a virus culture sample, a forensic sample, an infection sample, a nosocomial infection sample, a production sample, a drug preparation sample, a biological molecule production sample, a protein preparation sample, a lipid preparation sample, a carbohydrate preparation sample, a solution of a nucleotide, a solution of polynucleotide, a solution of a nucleic acid, a solution of a peptide, a solution of a polypeptide, a solution of an amino acid, a solution of a protein, a solution of a synthetic polymer, a solution of a biochemical composition, a solution of an organic chemical composition, a solution of an inorganic chemical composition, a solution of a lipid, a solution of a carbohydrate, a solution of a combinatory chemistry product, a solution of a drug candidate molecule, a solution of a drug molecule, a solution of a drug metabolite, a suspension of a cell, a suspension of a virus, a suspension of a microorganism, a suspension of a metal, a suspension of metal alloy, a solution of a metal ion, and any combination thereof.

* * * * *

```
                        SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
ctcatttcct ggtatgacaa cga                                         23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gtctacatgg caactgtgag gag                                         23

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
catggcaact gtgaggag                                               18
```